United States Patent
Reiser et al.

(10) Patent No.: US 12,326,457 B2
(45) Date of Patent: Jun. 10, 2025

(54) ICOSL FOR USE AS A RENAL THERAPEUTIC

(71) Applicant: Rush University Medical Center, Chicago, IL (US)

(72) Inventors: Jochen Reiser, Chicago, IL (US); Eunsil Hahm, Morton Grove, IL (US); Yanxia Cao, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 1104 days.

(21) Appl. No.: 17/057,474

(22) PCT Filed: May 23, 2019

(86) PCT No.: PCT/US2019/033800
§ 371 (c)(1),
(2) Date: Nov. 20, 2020

(87) PCT Pub. No.: WO2019/226922
PCT Pub. Date: Nov. 28, 2019

(65) Prior Publication Data
US 2021/0208163 A1    Jul. 8, 2021

Related U.S. Application Data

(60) Provisional application No. 62/676,070, filed on May 24, 2018.

(51) Int. Cl.
| | | |
|---|---|---|
| *A61P 13/12* | (2006.01) | |
| *C07K 14/705* | (2006.01) | |
| *C12Q 1/6883* | (2018.01) | |
| *G01N 33/68* | (2006.01) | |

(52) U.S. Cl.
CPC .......... *G01N 33/6893* (2013.01); *A61P 13/12* (2018.01); *C07K 14/70532* (2013.01); *C12Q 1/6883* (2013.01); *C12Q 2600/158* (2013.01); *G01N 2333/70546* (2013.01); *G01N 2800/347* (2013.01)

(58) Field of Classification Search
CPC .............................................. G01N 2800/347
See application file for complete search history.

(56) References Cited

U.S. PATENT DOCUMENTS

| | | | |
|---|---|---|---|
| 2006/0140944 A1* | 6/2006 | Yoshinaga | C07K 16/2827 435/69.7 |
| 2017/0320959 A1 | 11/2017 | Swanson et al. | |
| 2017/0334990 A1 | 11/2017 | Noelle et al. | |
| 2018/0085402 A1 | 3/2018 | Kahvejian et al. | |
| 2018/0110762 A1 | 4/2018 | Cox et al. | |

FOREIGN PATENT DOCUMENTS

| | | |
|---|---|---|
| WO | 2004073732 A1 | 9/2004 |
| WO | WO-2017181148 A2 * | 10/2017 ......... A61K 39/0011 |

OTHER PUBLICATIONS

Odobasic et al, Inducible co-stimulatory molecule ligand is protective during the induction and effector phases of crescentic glomerulonephritis. Journal of the American Society of Nephrology, (Apr. 2006) vol. 17, No. 4, pp. 1044-1053 (Year: 2006).*

Aicher A, et al. Characterization of human inducible costimulator ligand expression and function. J Immunol. 2000;164(9):4689-4696.

Barisoni L, Kriz W, Mundel P, D'Agati V. The dysregulated podocyte phenotype: a novel concept in the pathogenesis of collapsing idiopathic focal segmental glomerulosclerosis and HIV-associated nephropathy. J Am Soc Nephrol. 1999;10(1):51-61.

Bitzan M, Babayeva S, Vasudevan A, Goodyer P, Torban E. TNF-α pathway blockade ameliorates toxic effects of FSGS plasma on podocyte cytoskeleton and β3 integrin activation. Pediatr Nephrol. 2012;27(12):2217-2226.

Ernest S, Bello-Reuss E. Expression and function of P-glycoprotein in a mouse kidney cell line. Am J Physiol. 1995;269(2 pt 1):C323-C333.

Felding-Habermann B, Cheresh DA. Vitronectin and its receptors. Curr Opin Cell Biol. 1993;5(5):864-868.

Fogo AB. Mechanisms of progression of chronic kidney disease. Pediatr Nephrol. 2007;22(12):2011-2022.

Greenwald RJ, Freeman GJ, Sharpe AH. The B7 family revisited. Annu Rev Immunol. 2005;23:515-548.

Hahm E, et al. Bone marrow-derived immature myeloid cells are a main source of circulating suPAR contributing to proteinuric kidney disease. Nat Med. 2017;23(1):100-106.

Hall SS. Omen in the blood. Science. 2018;360(6386):254-258.

Hamel KM, Cao Y, Olalekan SA, Finnegan A. B cell-specific expression of inducible costimulator ligand is necessary for the induction of arthritis in mice. Arthritis Rheumatol. 2014;66(1):60-67.

Hayek SS, et al. A tripartite complex of suPAR, APOL 1 risk variants and αvβ3 integrin on podocytes mediates chronic kidney disease. Nat Med. 2017;23(8):945-953.

Hayek SS, et al. Soluble urokinase receptor and chronic kidney disease. N Engl J Med. 2015;373(20):1916-1925.

Hutloff A, et al. ICOS is an inducible T-cell co-stimulator structurally and functionally related to CD28. Nature. 1999;397(6716):263-266.

International Preliminary Report on Patentability, issued in PCT/US20219/033800, dated Nov. 24, 2020.

International Search Report, issued in PCT/US20219/033800, dated Sep. 17, 2019.

Kreidberg JA, Symons JM. Integrins in kidney development, function, and disease. Am J Physiol Renal Physiol. 2000;279(2):F233-F242.

(Continued)

*Primary Examiner* — Qiuwen Mi
(74) *Attorney, Agent, or Firm* — Barnes & Thornburg LLP

(57) ABSTRACT

Methods treating an aberrant activation of αvβ integrin are provided. The methods include administering a therapeutically effective amount of inducible co-stimulator ligand (ICOSL) polypeptide to a subject in need thereof. Methods of identifying subjects having a kidney injury are also provided.

6 Claims, 12 Drawing Sheets

Specification includes a Sequence Listing.

(56) References Cited

OTHER PUBLICATIONS

Lee HW, et al. Absence of miR-146a in podocytes increases risk of diabetic glomerulopathy via up-regulation of ErbB4 and Notch-1. J Biol Chem. 2017;292(2):732-747.

Ling V, et al. Cutting edge: identification of GL50, a novel B7-like protein that functionally binds to ICOS receptor. J Immunol. 2000;164(4):1653-1657.

Maile LA, et al. Blocking ligand occupancy of the αVβ3 integrin inhibits the development of nephropathy in diabetic bigs. Endocrinology. 2014;155(12):4665-4675.

Maile LA, Gollahon K, Wai C, Dunbar P, Busby W, Clemmons D. Blocking αVβ3 integrin ligand occupancy inhibits the progression of albuminuria in diabetic rats. J Diabetes Res. 2014;2014:421827.

Mundel P, et al. Rearrangements of the cytoskeleton and cell contacts induce process formation during differentiation of conditionally immortalized mouse podocyte cell lines. Exp Cell Res. 1997;236(1):248-258.

Odobasic D, Kitching AR, Semple TJ, Holdsworth SR. Inducible co-stimulatory molecule ligand is protective during the Induction and effector phases of crescentic glomerulonephritis. J Am Soc Nephrol. 2006; 17(4):1044-1053.

Ohtsubo K, Marth JD. Glycosylation in cellular mechanisms of health and disease. Cell. 2006;126(5):855-867.

Pozzi A, Zent R. Integrins in kidney disease. J Am Soc Nephrol. 2013;24(7):1034-1039.

Reiser J, Altintas MM. Podocytes. F1000Res. 2016;5(F1000 Faculty Rev):114.

Reiser J, et al. Induction of B7-1 in podocytes is associated with nephrotic syndrome. J Clin Invest. 2004;113(10):1390-1397.

Reiser J, Lee HW, Gupta V, Altintas MM. A high-content screening technology for quantitatively studying podocyte dynamics. Adv Chronic Kidney Dis. 2017;24(3):183-188.

Scholz et al., Renal Dendritic Cells Stimulate IL-10 Production and Attenuate Nephrotoxic Nephritis. J Am Soc Nephrol, 2008; 19(3):527-537.

Staeck O, et al. Recurrent primary focal segmental glomerulosclerosis managed with intensified plasma exchange and concomitant monitoring of soluble urokinase-type plasminogen activator receptor-mediated podocyte β3-integrin activation. Transplantation. 2015;99(12):2593-2597.

Swallow MM, Wallin JJ, Sha WC. B7h, a novel costimulatory homolog of B7.1 and B7.2, is induced by TNF-α. Immunity. 1999;11(4):423-432.

Takada Y, Ye X, Simon S. The integrins. Genome Biol. 2007;8(5):215.

Takemoto M, et al. A new method for large scale isolation of kidney glomeruli from mice. Am J Pathol. 2002;161 (3):799-805.

Tesch GH, Allen TJ. Rodent models of streptozotocin-induced diabetic nephropathy. Nephrology (Carlton). 2007;12(3):261-266.

Wang S, et al. Costimulation of T cells by B7-H2, a B7-like molecule that binds ICOS. Blood. 2000;96(8):2808-2813.

Wei C, et al. Circulating urokinase receptor as a cause of focal segmental glomerulosclerosis. Nat Med. 2011;17(8):952-960.

Wei C, et al. Modification of kidney barrier function by the urokinase receptor. Nat Med. 2008;14(1):55-63.

Yoo TH, et al. Sphingomyelinase-like phosphodiesterase 3b expression levels determine podocyte injury phenotypes in glomerular disease. J Am Soc Nephrol. 2015;26(1):133-147.

Yoshinaga SK, et al. T-cell co-stimulation through B7RP-1 and ICOS. Nature. 1999;402(6763):827-832.

Zhou X, et al. An integrin antagonist (MK-0429) decreases proteinuria and renal fibrosis in the ZSF1 rat diabetic nephropathy model. Pharmacol Res Perspect. 2017;5(5):e00354.

Ria et al., "Alpha(v)beta(3) integrin engagement enhances cell invasiveness in human multiple myeloma," Haematologica, 2002; 87(8):836-845.

* cited by examiner

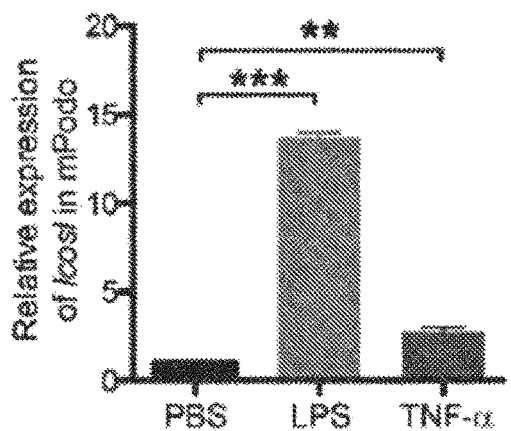
FIG. 1C Mouse podocyte cell line
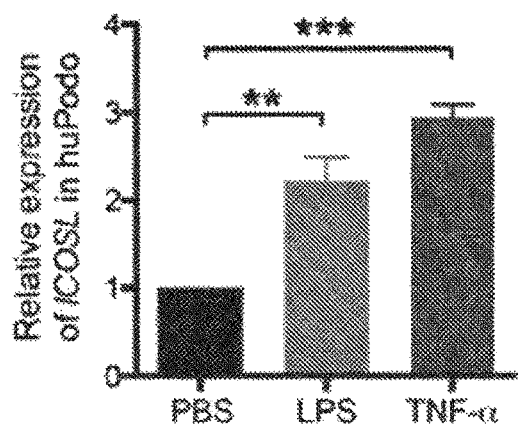
FIG. 1D Human podocyte cell line
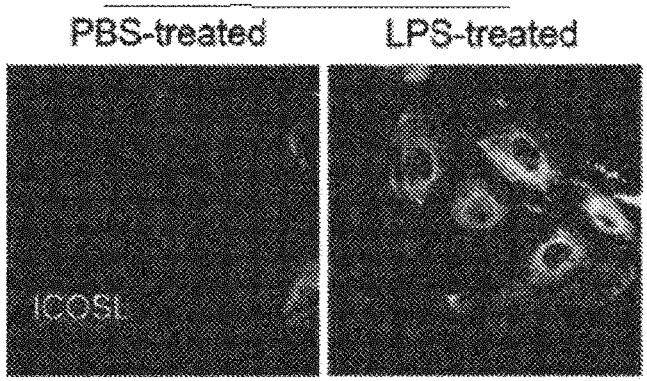
FIG. 1E Human podocyte cell line
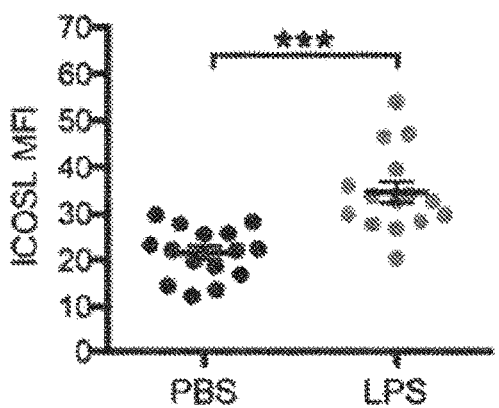
FIG. 1F
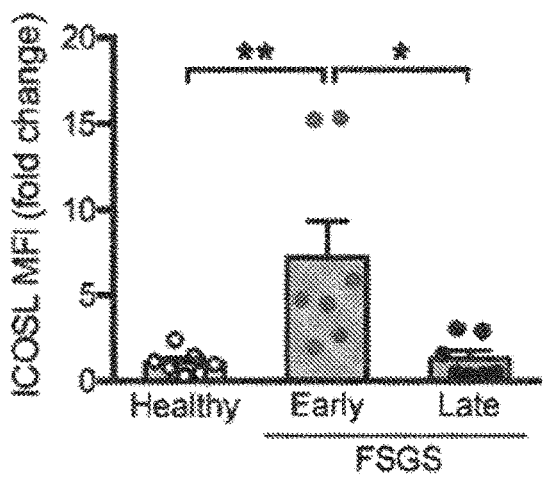
FIG. 1H Glomerular ICOSL
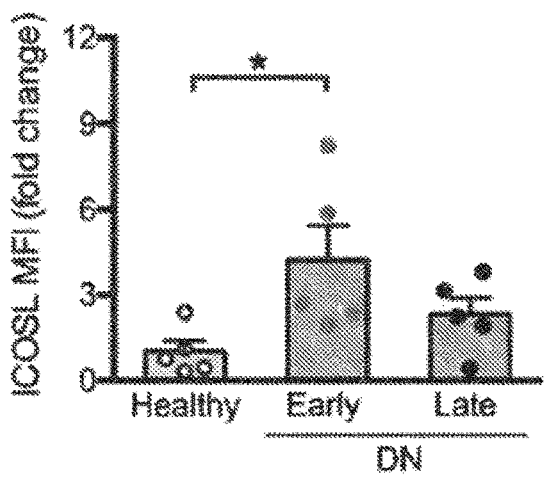
FIG. 1I Glomerular ICOSL

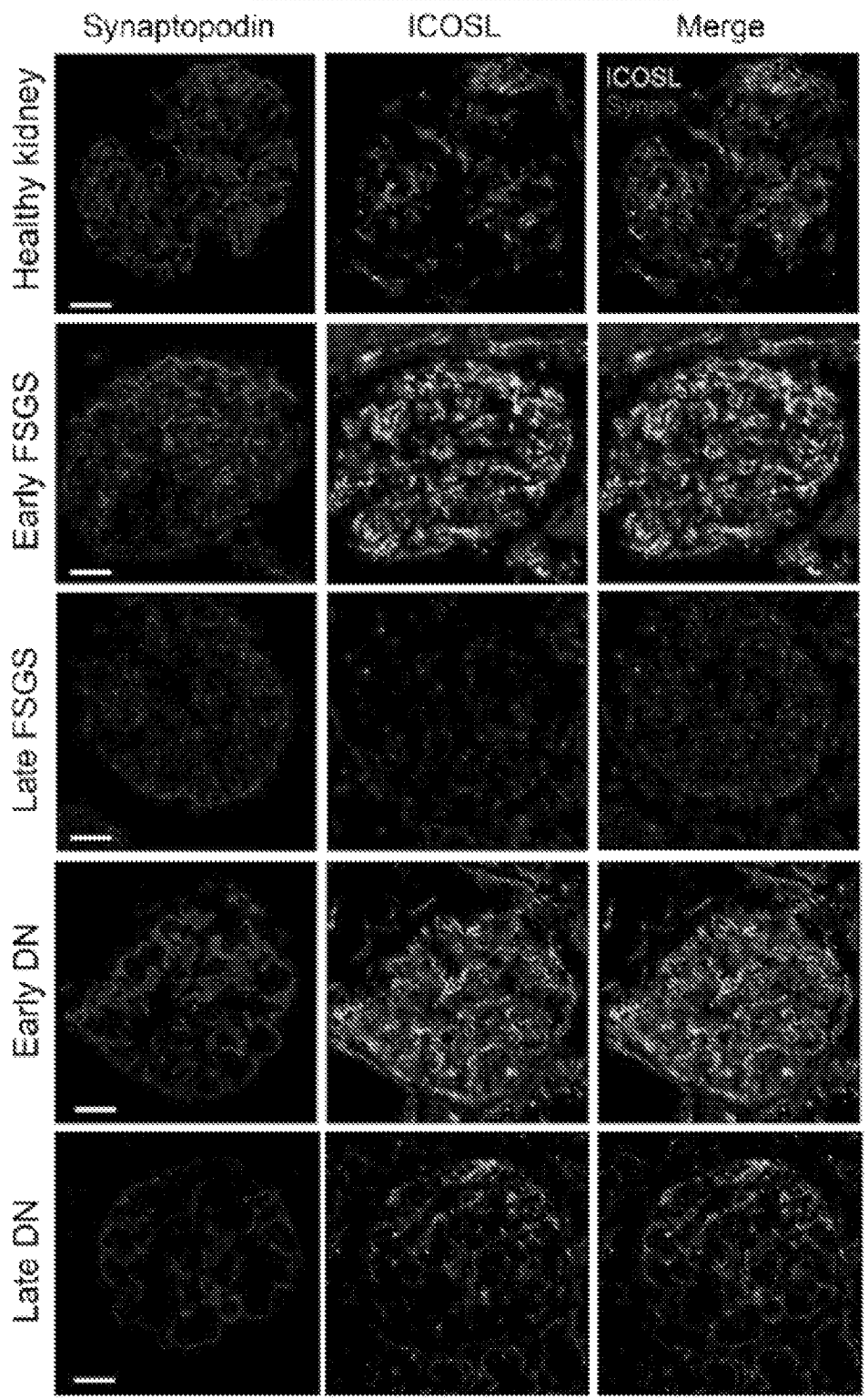

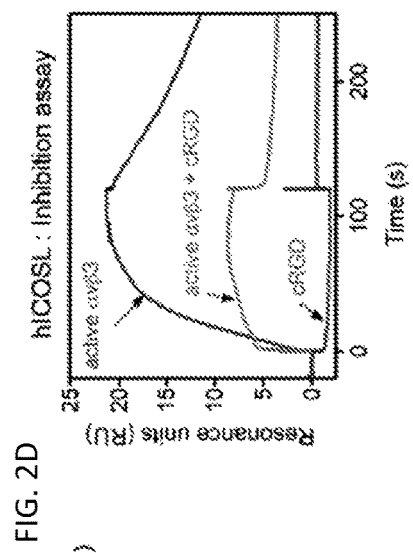
FIG. 2A
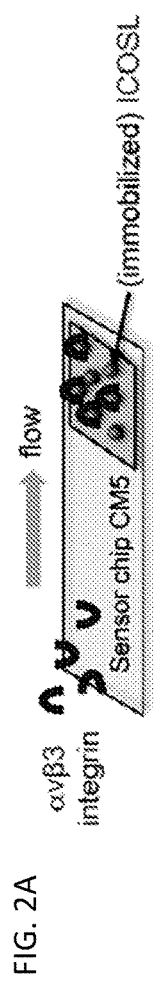
FIG. 2B
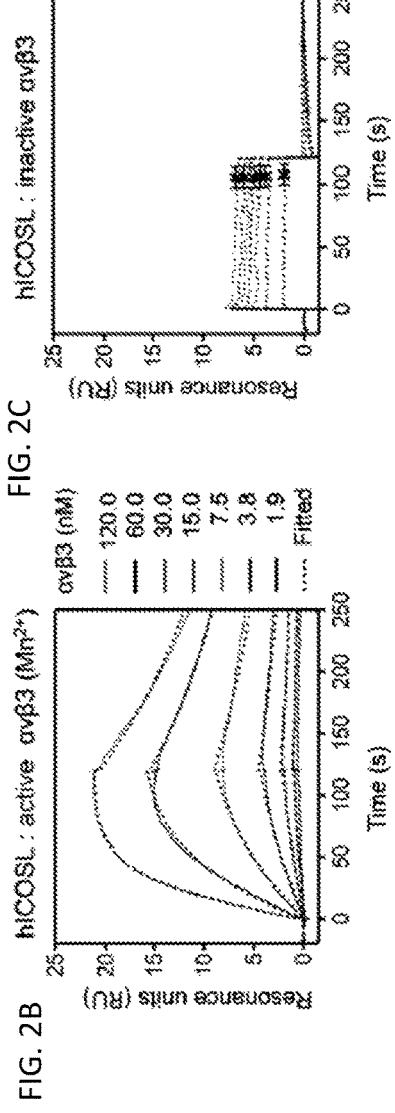
FIG. 2C
FIG. 2D

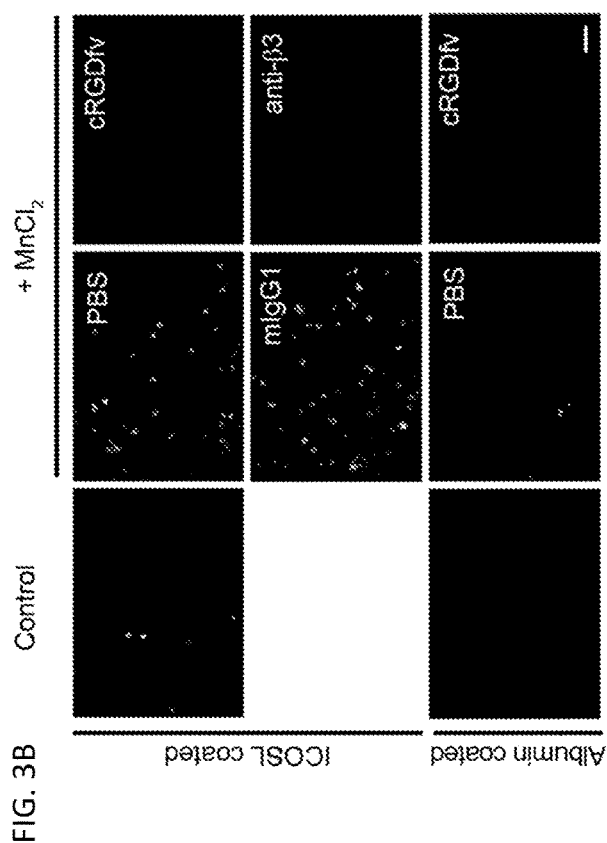
FIG. 3A
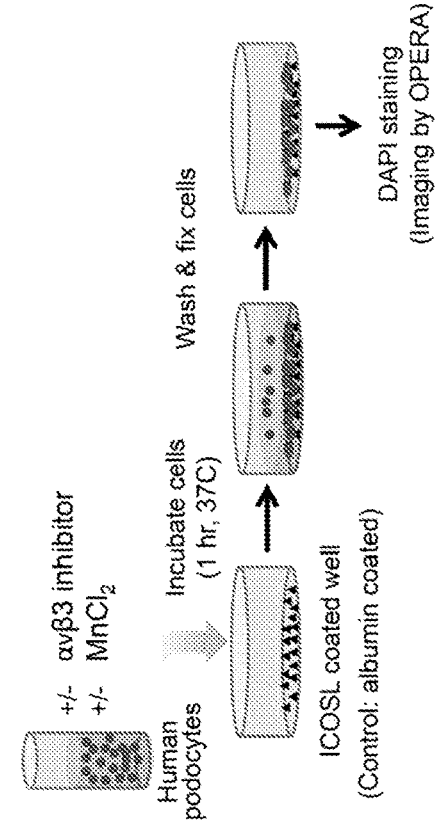
FIG. 3B
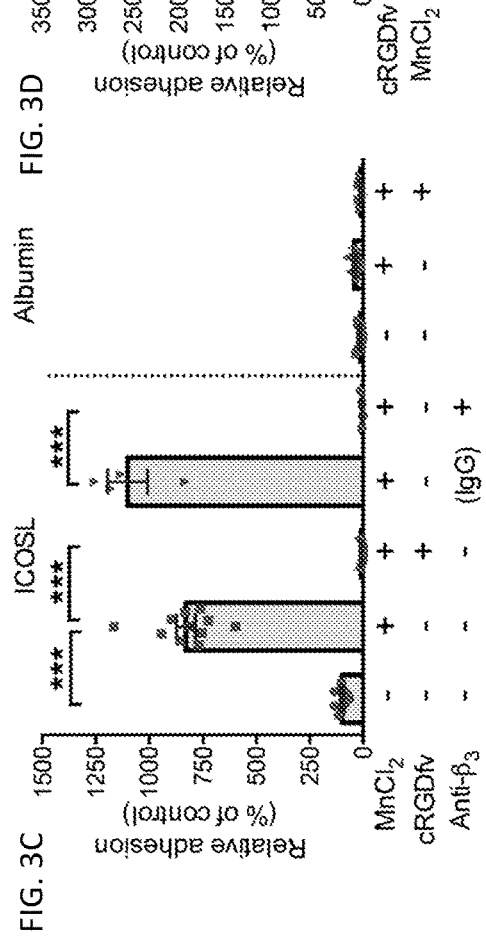
FIG. 3C
FIG. 3D

ICOSL FOR USE AS A RENAL THERAPEUTIC

RELATED APPLICATIONS

This application is a National Stage application of International Application No. PCT/US2019/033800, filed May 23, 2019, which claims the benefit of U.S. Provisional Application No. 62/676,070, filed May 23, 2018, both of which are incorporated by reference herein in their entirety.

SEQUENCE LISTING

The instant application contains a Sequence Listing which has been submitted electronically in ASCII format and is hereby incorporated by reference in its entirety. The ASCII copy, created on May 22, 2019, is named 14904-481 Sequence listing_ST25.txt and is 7 KB in size.

BACKGROUND

1. Technical Field Text

The present disclosure relates to methods for treating aberrant activation of $\alpha v \beta 3$ integrin, and in particular methods including administration of inducible co-stimulator ligand (ICOSL).

2. Background Information

Integrins are heterodimeric transmembrane glycoproteins that facilitate cellular attachment to the extracellular matrix or to ligands on other cells, and mediate multiple cellular processes such as proliferation, differentiation, adhesion, and migration (1). In the kidney, integrins are known to play critical roles in organ development, homeostasis, and renal disease progression (2, 3). Early glomerular injury involves a morphological change to podocytes, the terminally differentiated glomerular cells that are essential for kidney filtration, called foot process effacement (fusion), and often leads to proteinuria, a hallmark of many kidney diseases (4, 5). Activation of $\alpha v \beta 3$ integrin on podocytes has been implicated in the pathogenesis of proteinuric kidney diseases such as focal and segmental glomerulosclerosis (FSGS), diabetic nephropathy (DN), and potentially several other renal diseases (6-11). In line with these findings, blocking of $\alpha v \beta 3$ activation via antagonist treatment has been shown to significantly reduce proteinuria, kidney fibrosis, and subsequent disease progression in animal models (6, 7, 12-14).

Inducible costimulator ligand (ICOSL) (also known as B7h, GL50, B7RP-1, and B7-H2) belongs to the B7 superfamily of proteins that bind to the CD28 family of receptors on lymphocytes (15-19). ICOSL is expressed primarily by professional antigen presenting cells (APCs) such as B cells, dendritic cells, and macrophages. Similar to other members of the CD28/B7 superfamily, binding of ICOSL on APCs to ICOS on T cells leads to costimulatory signaling, resulting in multiple T cell functions (15, 17, 20). A previous publication exploring a potential functional role for the ICOS/ICOSL pathway in the kidney reported that ICOSL is induced in nephritic glomeruli (21). This leads to a local reduction of T cell and macrophage accumulation and attenuated renal injury, suggesting a protective role (21). Similarly, Icosl mRNA expression has been detected in some murine nonlymphoid tissues, such as kidney and testis, following lipopolysaccharide (LPS) injection (15). However, given that ICOS and ICOSL have been considered an exclusively single receptor-ligand pair (17, 22), little is known about ICOS-independent cellular functions between ICOSL and any yet-to-be identified corresponding receptors.

In this study, we showed that ICOSL could directly bind and counter the negative effects of activated $\alpha v \beta 3$ integrin on podocytes. An in silico sequence analysis of human and mouse ICOSL proteins, followed by 3-dimensional (3D) homology protein modeling, revealed that both human and mouse ICOSL contain an Arg-Gly-Asp (RGD) motif at an exposed loop region. Using surface plasmon resonance (SPR) combined with competition assays, we showed that ICOSL, through its RGD motif, directly bound $\alpha v \beta 3$ integrin. Icosl–/– (Icosl-KO) mice were significantly more susceptible than control mice to LPS-induced proteinuria and STZ-induced DN phenotypes. Bone marrow (BM) transplant experiments revealed that ICOSL's protective abilities arise from its nonhematopoietic expression. Finally, administration of ICOSL protein to Icosl-KO mice reduced their susceptibility to LPS-induced proteinuria. Taken together, this disclosure shows a new role for ICOSL in countering activated $\alpha v \beta 3$ integrin. This disclosure shows a role for endogenous integrin antagonists for use as therapies for diseases that stem from aberrant integrin signaling.

BRIEF SUMMARY

Methods treating an aberrant activation of $\alpha v \beta 3$ integrin are provided. The methods include administering a therapeutically effective amount of inducible co-stimulator ligand (ICOSL) polypeptide to a subject in need thereof.

Methods of identifying subjects having a kidney injury are also provided. The methods include measuring a level of ICOSL in a biological sample from the subject relative to a level of ICOSL in a control subject free of kidney injury.

BRIEF DESCRIPTION OF THE DRAWINGS

FIGS. 1A-1I illustrate that increased ICOSL expression is an early cellular response to renal injury.

Relative mRNA expression values measured by quantitative PCR targeting ICOSL in both mouse (A-C; mPodo) and human (D; hPodo) podocyte cell lines. (FIG. 1A) qPCR analysis of Icosl mRNA in mouse podocyte cell lines 1, 3, or 6 hours after 50 µg/ml LPS treatment, normalized with the expression level of Gapdh and presented relative to the expression of Icosl in untreated control cells. (FIG. 1B) Primary podocyte isolation from BALB/c mice by Dynabead perfusion followed by 50 µg/ml LPS treatment for 3 hours. The cells were cultured and harvested, and relative expression levels of Icosl were measured by qPCR. (FIG. 1C) Relative mRNA expression levels of Icosl in mouse podocyte cell lines treated with 50 µg/ml LPS or 100 ng/ml TNF-α for 3 hours. (FIG. 1D) Relative expression levels of ICOSL in human podocyte cell lines following the same treatments as in C. Representative images (FIG. 1E) and quantification (FIG. 1F) of immunofluorescence staining of ICOSL protein in human podocytes treated with 50 µg/ml LPS or PBS as control. For quantification, cells were individually defined by tracing cell borders, and the levels of ICOSL protein expression were measured by mean fluorescence intensity (MFI) using ImageJ software (n=15 cells/group). (FIGS. 1G-1I) Human kidney biopsy samples were double-stained to detect ICOSL (green) and synaptopodin (Synpo; red) by immunofluorescence staining. As depicted, analysis groups include healthy control and kidney tissues from patients with FSGS or DN at early/late stages (n=5/group). The confocal micrographs were analyzed for glomerular expression of ICOSL by manually selecting glomeruli, defined by synaptopodin, as the region of interest. Representative confocal microscopic images are shown in FIG. 1G. Scale bars, 50 μm. ICOSL MFI in FSGS (FIG. 1H) or DN (FIG. 1I) groups was normalized to that of healthy controls, and data are presented as fold changes. Data are shown as mean±SEM; *P<0.05, P<0.01, *P<0.001; 1-way ANOVA with Dunnett's multiple comparison test (FIGS. 1A, 1C, and 1D) or with Tukey's multiple comparison test (FIGS. 1H and 1I) and Student's 2-tailed, unpaired t test (FIGS. 1B and 1F).

FIGS. 2A-2I illustrate that ICOSL binds to active $\alpha v \beta 3$ integrin through its RGD motif.

ICOSL binds to active $\alpha v \beta 3$ integrin through its RGD motif. (FIG. 2A) Schematic of a gold surface with ICOSL protein on a sensor chip CM5 and associated protein ($\alpha v \beta 3$ integrin) over which buffer is flown in SPR assay. (FIGS. 2B-2I) SPR sensorgrams depicting interaction of immobilized human ICOSL (hICOSL, FIGS. 2B-2D) or mouse ICOSL (mICOSL, FIGS. 2E-2I) with $\alpha v \beta 3$ integrin. These bindings were tested in the presence (FIGS. 2B and 2E, active form of $\alpha v \beta 3$) or absence (FIGS. 2C and 2F, inactive form of one with EDTA in the binding buffer) of Mn2+. (FIGS. 2D and 2G) SPR used in an inhibition experiment with cRGDfv. Injection of $\alpha v \beta 3$ integrin only (FIG. 2D, 120 nM $\alpha v \beta 3$ or G, 150 nM $\alpha v \beta 3$) resulted in a binding signal for immobilized hICOSL or mICOSL alone (pink line). Preincubation with cRGDfv (3 UM or 15 UM) significantly reduced the binding for ICOSL, indicating that the RGD peptide competes with ICOSL for binding to $\alpha v \beta 3$ (orange line). cRGDfv alone was used as a control (green line). (FIGS. 2H and 2I) SPR sensorgrams showing the binding between WT (FIG. 2H) or mutant (FIG. 2I) mICOSL protein and $\alpha v \beta 3$ integrin in the presence of physiologically relevant divalent ions, Ca2+ (0.2 mM) and Mg2+ (0.1 mM). The average KD values were determined from at least 3 independent experiments. Rate constants (ka and kd) were determined by kinetic fitting (black dotted line) of the sensorgrams using 1-to-1 Langmuir binding equation, and KD values for FIGS. 2B, 2E, and 2H were calculated by kd/ka (B, KD=16.2±4.0 nM for hICOSL/$\alpha v \beta 3$ with Mn2+; FIG. 2E, KD=24.2±6.5 nM for mICOSL/$\alpha v \beta 3$ with Mn2+; FIG. 2H, KD=21.3±1.2 nM for WT mICOSL/$\alpha v \beta 3$ with Ca2+/Mg2+). KD values for FIGS. 2C, 2F, and 2I were calculated from steady-state affinity fittings (FIG. 2C, KD=411.8±164.1 nM for hICOSL/$\alpha v \beta 3$; FIG. 2F, KD≥2 mM for mICOSL/$\alpha v \beta 3$; FIG. 2I, KD=0.83±0.8 mM for mutant mICOSL/$\alpha v \beta 3$ with Ca2+/Mg2+).

FIGS. 3A-3D illustrate that ICOSL regulates $\alpha v \beta 3$ integrin-dependent adhesion in human podocytes.

(FIG. 3A) Schematic representation of the protocol to measure relative cell adhesion levels in cultured human podocytes. Image analysis and quantification by high-content screening technology were described in Methods. (FIG. 3B) Phase-contrast microscopy images show that cultured human podocytes confer enhanced adhesion to ICOSL mediated by 33 integrin treated with Mn2+, but do not adhere on albumin (protein control). Increased adhesion levels were completely prevented by incubation with the integrin inhibitors, including cRGD peptide and anti-$\beta 3$ integrin antibody. Scale bar 100 μm. (FIG. 3C) Quantification of the cell adhesion using the images in B. ICOSL induced cell adhesion to RGD-dependent 33 integrin on cultured podocytes. (FIG. 3D) Cell adhesion analysis of cultured podocytes plated on vitronectin. Data are shown as mean±SD; ***P<0.001; 1-way ANOVA with Tukey's multiple comparison test (C and D).

(FIGS. 4A and 4B), BALB/c WT and Icosl-KO mice were injected with either PBS or LPS (2.5 mg/kg body weight), then urine and blood were collected 24 hours later (n=10 for WT PBS, n=10 for WT LPS, n=14 for KO PBS, n=14 for KO LPS). (FIG. 4A) Urinary albumin and creatinine were measured using a mouse albumin ELISA kit and a creatinine assay kit, respectively. ACR ratio (mg/g) was calculated and used as a parameter to determine proteinuria. (FIG. 4B) Renal function was evaluated by measuring BUN levels as described in Methods. (FIGS. 4C and 4D) Both BALB/c WT (black dots) and Icosl-KO (red dots) mice developed hyperglycemia after STZ injection (n=5-6 per group). (FIG. 4C) The floating bar graph indicates urinary albumin excretion levels. (FIG. 4D) BUN levels. (FIG. 4E) Transmission electron microscope (TEM) analysis of PFA-fixed kidney glomeruli from STZ-induced WT and Icosl-KO mice (14 weeks after STZ injection). Top, TEM images displaying capillary loops at ×5000 magnification. Bottom, high magnification of podocyte foot processes (×15,000) highlighting mild effacement in the WT group and more severe effacement in the Icosl-KO group. Scale bars, 2 μm. (FIG. 4F) Quantification of foot process (FP) effacement using the TEM images (FIG. 4E). Boxes and line represent mean±SEM and whiskers showing minimum and maximum points (n=10 biological samples per group). Data are mean±SEM; *P<0.05, P<0.01, *P<0.001; 1-way ANOVA with Tukey's multiple comparison test (FIGS. 4A and 4B) or multiple unpaired t test with the Holm-Sidak comparisons test (FIGS. 4C and 4D) or Student's 2-tailed, unpaired t test (FIG. 4F).

(FIG. 5A) Schematic experimental design for BM chimeric mice generation. In brief, BM cells were isolated from donor mice (WT and Icosl-KO) and then transferred into irradiated recipient mice (WT and Icosl-KO) on day 0. The 4 types of BM chimera mice were produced: WT donor cells into WT recipients, WT donor cells into KO recipients, KO donor cells into WT recipients, and KO donor cells into KO recipients. Six weeks after engraftment, the BM chimeric mice were injected with LPS (2 mg/kg body weight). (FIG. 5B) Urine was harvested from each group of mice 24 hours after LPS administration (n=5-7 per group from 2 independent experiments). Data are mean±SEM; *P<0.05, ***P<0.001; 1-way ANOVA with Tukey's multiple comparison test.

Schematic representation of the experimental design (FIG. 6A). In brief, Icosl-KO mice were challenged with 2.5 mg/kg LPS, then injected intravenously (i.v.) with mouse ICOSL protein (1 mg/kg) or BSA (1 mg/kg) as a protein control 1 and 12 hours after LPS injection. Urine samples were collected at time points, 0, 12, and 24 hours after LPS administration for ACR measurement. (FIG. 6B) ACR levels in Icosl-KO mice treated with either ICOSL protein (blue dots) or BSA (red dots) (n=12 per group from 2 independent experiments). Schematic representation of the experimental design (FIG. 6C). Icosl-KO mice were challenged with 2.5 mg/kg LPS, then injected i.v. with either WT (RGD) or mutant (AAA) mouse ICOSL protein (1 mg/kg) 1 hour after LPS injection. (FIG. 6D) ACR levels in Icosl-KO mice treated with either WT (blue dots) or mutant (red dots) ICOSL (n=5 per group from 1 experiment). Data are mean±SEM; *P<0.05, ***P<0.001; multiple unpaired t test with the Holm-Sidak comparisons test (FIGS. 6B and 6D).

In this study, it is shown that ICOSL binds podocyte αvβ3 integrin through its RGD motif. Kidney injury results in a rapid increase of ICOSL expression, leading to podocyte protection by blocking active αvβ3 integrin. ICOSL acts as a regulatory brake to modulate active αvβ3 integrin-mediated signaling. Fp, foot process.

Figure 8A:
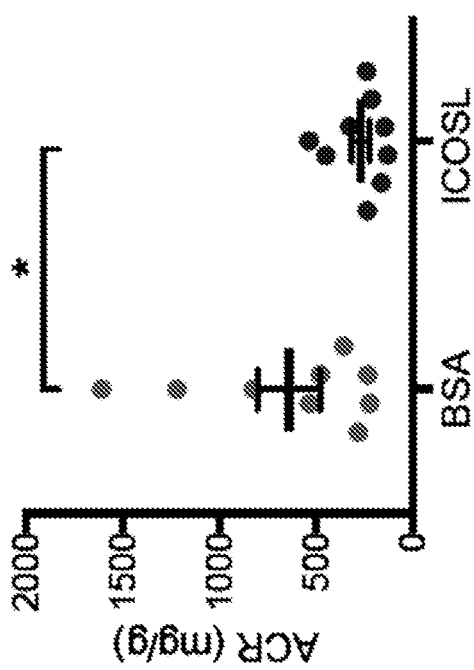
Figure 8B:
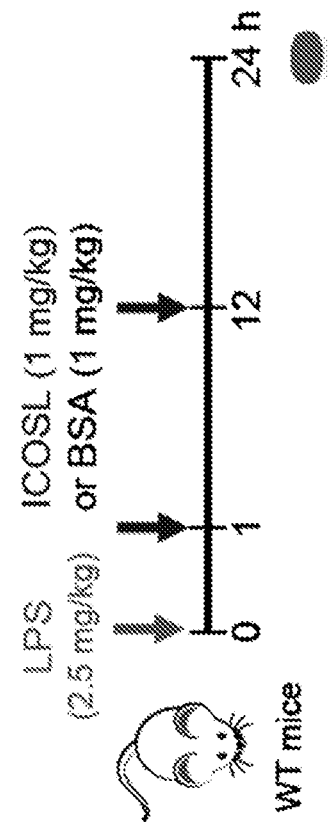

FIGS. 8A-8B illustrate that administration of ICOSL WT reduces proteinuria in LPS injected WT mice. BALB/c WT mice were challenged with 2.5 mg/kg LPS, then intravenously injected with mouse ICOSL protein (1 mg/kg) or BSA (1 mg/kg) as a protein control 1 and 12 hours after LPS injection. Urine samples were collected before injection then 12 and 24 hours after LPS administration. Schematic representation of the experimental design (FIG. 8A) and ACR levels (FIG. B) in WT mice injected with ICOSL protein or BSA 24 hours after LPS injection (n=9 per group from two independent experiments). Data are mean±SEM; *P<0.05; Student's two-tailed, unpaired t test.

Figure 9:
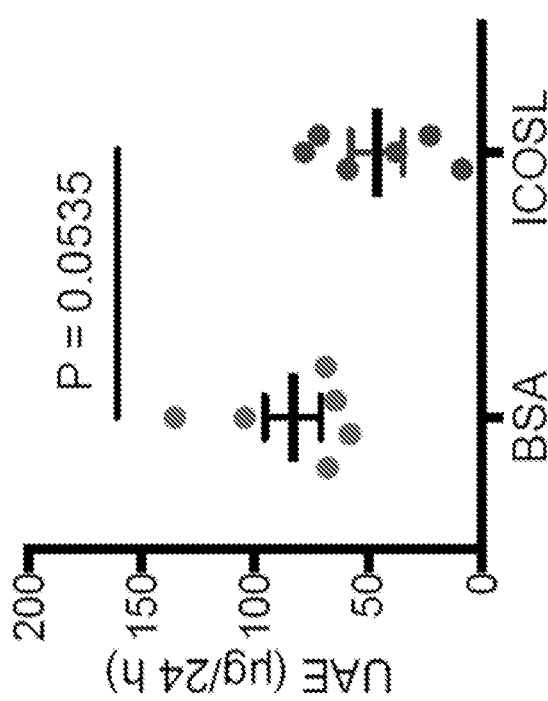

FIG. 9 illustrates that ICOSL treatment had a trend toward lower proteinuria in STZ-induced DN mice. Urinary albumin excretion (UAE) for 24 hours in ICOSL KO mice treated either with ICOSL protein or BSA (n=6 per group from one experiment). In brief, male ICOSL KO mice were challenged with STZ to induce diabetes. Two weeks after STZ injection, the mice were divided into 2 groups. Each group (n=6 per group) was treated with either mouse ICOSL protein (1 mg/kg, i.p., twice/week) or BSA as a protein control for 4 weeks. For the measurement of urinary albumin excretion, urine samples were collected using metabolic cages at 6 weeks after STZ administration (ICOSL/BSA treatment for 4 weeks). Data are mean±SEM; Student's two-tailed, unpaired t test.

DETAILED DESCRIPTION

The embodiments disclosed below are not intended to be exhaustive or to limit the scope of the disclosure to the precise form in the following description. Rather, the embodiments are chosen and described as examples so that others skilled in the art may utilize its teachings. Unless otherwise defined, all technical and scientific terms used herein have the same meaning as commonly understood by one of ordinary skill in the art to which this disclosure pertains. In case of conflict, the present document, including definitions, will control.

The uses of the terms "a" and "an" and "the" and similar references (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the disclosure and does not pose a limitation on the scope unless otherwise claimed. No language in the specification should be construed as indicating any non-claimed element as essential to the practice of the embodiments.

As used herein, the term "amount" refers to "an amount effective" or "therapeutically effective amount" of a composition, e.g., antibody or peptide, to achieve a beneficial or desired prophylactic or therapeutic result, including clinical results. A "therapeutically effective amount" of a composition may vary according to factors such as the disease state, age, sex, and weight of the individual, and the ability of the antibody or peptide to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient). When a therapeutic amount is indicated, the precise amount of the compositions of the present disclosure to be administered may be determined by a physician with consideration of individual differences in age, weight, tumor size, extent of infection or metastasis, and condition of the patient (subject).

Inducible Co-Stimulator Ligand (ICOSL) Polypeptides

In some embodiments, ICOSL compositions and methods of using ICOSL are described herein. In some embodiments, ICOSL polypeptides may be used as therapies for diseases that stem from aberrant integrin signaling, and in some embodiments, ICOSL polypeptides may be used in countering activated αvβ3 integrin. As used herein ICOSL polypeptides refer to full length ICOSL polypeptide and active fragments of ICOSL polypeptide. Full length ICOSL polypeptide is shown below in SEQ ID NO: 1 (human). In some embodiments, the signal peptide of amino acid residues 1-18 may be removed from the full length ICOSL polypeptide of SEQ ID NO: 1 either in vitro or in vivo and used therapeutically. In some embodiments, the extracellular domain including amino acids 1-258 of the full length ICOSL polypeptide of SEQ ID NO: 1 may be used. Additional active ICOSL polypeptide fragments including the RGD sequence may also be used.

```
                                            (SEQ ID NO: 1)
MRLGSPGLLF  LLFSSLRADT  QEKEVRAMVG  SDVELSCACP

EGSRFDLNDV  YVYWQTSESKTVVTYHIPQN  SSLENVDSRY

RNRALMSPAG  MLRGDFSLRL  FNVTPQDEQK

FHCLVLSQSLGFQEVLSVEV  TLHVAANFSV  PVVSAPHSPS

QDELTFTCTS  INGYPRPNVY  WINKTDNSLLDQALQNDTVF

LNMRGLYDVV  SVLRIARTPS  VNIGCCIENV  LLQQNLTVGS

QTGNDIGERDKITENPVSTG  EKNAATWSIL  AVLCLLVVVA

VAIGWVCRDR  CLQHSYAGAW  AVSPETELTG  HV
```

(ICOSL human UniProtKB-O75144) (SEQ ID NO: 1) Any of the three isoforms of human ICOSL described for UniProtKB-O75144 may be used.

Murine full length ICOSL polypeptide is shown in SEQ ID NO: 2 below.

```
                                            (SEQ ID NO: 2)
MQLKCPCFVS  LGTRQPVWKK  LHVSSGFFSG  LGLFLLLLSS

LCAASAETEV  GAMVGSNVVL  SCIDPHRRHF  NLSGLYVYWQ
```

```
IENPEVSVTY YLPYKSPGIN VDSSYKNRGH

LSLDSMKQGNFSLYLKNVTP QDTQEFTCRV FMNTATELVK

ILEEVVRLRV AANFSTPVIS TSDSSNPGQE RTYTCMSKNG

YPEPNLYWIN TTDNSLIDTA LQNNTVYLNK LGLYDVISTL

RLPWTSRGDV LCCVENVALH QNITSISQAE SFTGNNTKNP

QETHNNELKV LVPVLAVLAA AAFVSFIIYR RTRPHRSYTG

PKTVQLELTD HA
```

ICOSL mouse (UniProtKB-Q9JHJ8). Either of the two isoforms of mouse ICOSL described for UniProtKB-Q9JHJ8 may be used.

In some embodiments, the ICOSL polypeptides described herein may be used to treat disorders that include, but are not limited to the following: podocyte diseases or disorders, proteinuria, glomerular diseases, membranous glomerulonephritis, focal segmental glomerulonephritis, minimal change disease, nephrotic syndromes, pre-eclampsia, eclampsia, kidney lesions, collagen vascular diseases, stress, strenuous exercise, benign orthostatic (postural) proteinuria, focal segmental glomerulosclerosis (FSGS), IgA nephropathy, IgM nephropathy, membranoproliferative glomerulonephritis, membranous nephropathy, sarcoidosis, Alport's syndrome, diabetes mellitus, kidney damage due to drugs, Fabry's disease, infections, aminoaciduria, Fanconi syndrome, hypertensive nephrosclerosis, interstitial nephritis, Sickle cell disease, hemoglobinuria, multiple myeloma, myoglobinuria, diabetic nephropathy (DN), lupus nephritis, Wegener's Granulomatosis or Glycogen Storage Disease Type 1. In some embodiments, the ICOSL polypeptides may be used to treat acute or chronic kidney injury. In some embodiments, ICOSL expression is used to identify early kidney injury. Early cellular response and early kidney injury can be defined by podocyte foot process effacement, reduced synaptopodin expression, and increased ICOSL expression.

Recombinant Expression Vectors and Host Cells

In some embodiments, vectors, for example, recombinant expression vectors, containing a nucleic acid encoding ICOSL are disclosed. The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Examples of vectors are plasmids (e.g., DNA plasmids or RNA plasmids), autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or PI-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pCIneo vectors (Promega) for expression in mammalian cells; pLenti4N5-DEST™, pLenti6N5-DEST™, and pLenti6.2N5-GW/lacZ (Invitrogen) for lentivirus-mediated gene transfer and expression in mammalian cells. In certain embodiments, useful viral vectors include, e.g., replication defective retroviruses and lentiviruses.

The term "viral vector" may refer either to a virus (e.g., a transfer plasmid that includes virus-derived nucleic acid elements that typically facilitate transfer of the nucleic acid molecule or integration into the genome of a cell; e.g. virus-associated vector), or viral particle capable of transferring a nucleic acid construct into a cell, or to the transferred nucleic acid itself. Constructs may be integrated and packaged into non-replicating, defective viral genomes like Adenovirus, Adeno-associated virus (AAV), or Herpes simplex virus (HSV) or others, including retroviral and lentiviral vectors, for infection or transduction into cells. The vector may or may not be incorporated into the cell's genome. Viral vectors and transfer plasmids contain structural and/or functional genetic elements that are primarily derived from a virus. Exemplary viruses used as vectors include retroviruses, adenoviruses, adeno-associated viruses, lentiviruses, pox viruses, alphaviruses, and herpes viruses. For example, the term "retroviral vector" refers to a viral vector or plasmid containing structural and functional genetic elements, or portions thereof, that are primarily derived from a retrovirus; the term "lentiviral vector" refers to a viral vector or plasmid containing structural and functional genetic elements, or portions thereof, including LTRs that are primarily derived from a lentivirus. The term "hybrid vector" refers to a vector, LTR or other nucleic acid containing both retroviral, e.g., lentiviral, sequences and non-lentiviral viral sequences. In one embodiment, a hybrid vector refers to a vector or transfer plasmid comprising retroviral e.g., lentiviral, sequences for reverse transcription, replication, integration and/or packaging.

The recombinant expression vectors can include a nucleic acid encoding a ICOSL described herein in a form suitable for expression of the nucleic acid in a host cell, which means that the recombinant expression vectors include one or more regulatory sequences, selected on the basis of the host cells to be used for expression, which is operatively linked to the nucleic acid sequence to be expressed.

To perform the treatment described herein, ICOSL polypeptides as described herein can be administered to a subject in need of the treatment via a suitable route. The ICOSL polypeptide can be administered to a subject in need of the treatment directly or indirectly (e.g., via one or more expression vectors adapted for expressing the ICOSL polypeptide). Such an expression vector can be constructed by inserting one or more nucleotide sequences of ICOSL into a suitable expression vector, in which the ICOSL sequences are in operable linkage with a suitable promoter.

The term "therapeutic effect" as used herein means an effect which induces, ameliorates or otherwise causes an improvement in the pathological symptoms, disease progression or physiological conditions associated with or resistance to succumbing to a disorder, for example a renal disorder, of a human or veterinary patient. The term "therapeutically effective amount" as used with respect to a drug means an amount of the drug which imparts a therapeutic effect to the human or veterinary patient.

Pharmaceutical Compositions

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al, (2003) New Engl. J. Med. 348:601-608; Milgrom et al, (1999) New Engl. J. Med. 341:1966-1973; Slamon et al, (2001) New Engl. J. Med. 344:783-792; Beniaminovitz et al, (2000) New Engl. J. Med. 342:613-619; Ghosh et al, (2003) New Engl. J. Med. 348:24-32; Lipsky et al, (2000) New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts. Compositions comprising binding agents such as antibodies or fragments thereof can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µ/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 25 mg/kg, at least 30 mg/kg, at least 40 mg/kg or at least 50 mg/kg (see, e.g., Yang et al, (2003) New Engl. J. Med. 349:427-434; Herold et al, (2002) New Engl. J. Med. 346:1692-1698; Liu et al, (1999) J. Neurol. Neurosurg. Psych. 67:451-456; Portielji et al, (2003) Cancer Immunol. Immunother. 52:133-144).

An effective amount for a particular patient may vary depending on factors such as the condition being treated, the overall health of the patient, the method route and dose of administration and the severity of side effects (see, e.g., Maynard et al., (1996) A Handbook of SOPs for Good Clinical Practice, Interpharm Press, Boca Raton, Fla.; Dent (2001) Good Laboratory and Good Clinical Practice, Urch PubL, London, UK).

The route of administration may be by, e.g., topical or cutaneous application, injection or infusion by intravenous, intraarticular, intraperitoneal, intracerebral, intramuscular, intraocular, intraarterial, intracerebrospinal, intralesional, or by sustained release systems or an implant (see, e.g., Sidman et al., (1983) Biopolymers 22:547-556; Langer et al., (1981) J. Biomed. Mater. Res. 15:167-277; Langer (1982) Chem. Tech. 12:98-105; Epstein et al, (1985) Proc. Natl. Acad. Sci. USA 82:3688-3692; Hwang et al., (1980) Proc. Natl. Acad. Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985, 320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

Methods for co-administration or treatment with a second therapeutic agent, e.g., a cytokine or steroid by way of non-limiting example, are known in the art (see, e.g., Hardman et al., (eds.) (2001) Goodman and Gilman's The Pharmacological Basis of Therapeutics, IO.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%>; at least 40%>, or at least 50%.

Additional therapies (e.g., prophylactic or therapeutic agents), which can be administered in combination with the agent described herein may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies or fragments thereof of the invention. The two or more therapies may be administered within one same patient visit.

The ICOSL agents and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the agents can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al); mannosides (Umezawa et al, (1988) Biochem. Biophys. Res. Commun. 153:1038); antibodies (Bloeman et al, (1995) FEBS Lett. 357:140; Owais et al., (1995) Antimicrob. Agents Chemother. 39:180); surfactant protein A receptor (Briscoe et al, (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The therapies (e.g., prophylactic or therapeutic agents) of the combination therapies can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof of the invention are administered to a subject in a sequence and within a time interval such that the antibodies of the invention can act together with the other therapy (ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

Results

Figure 1B:
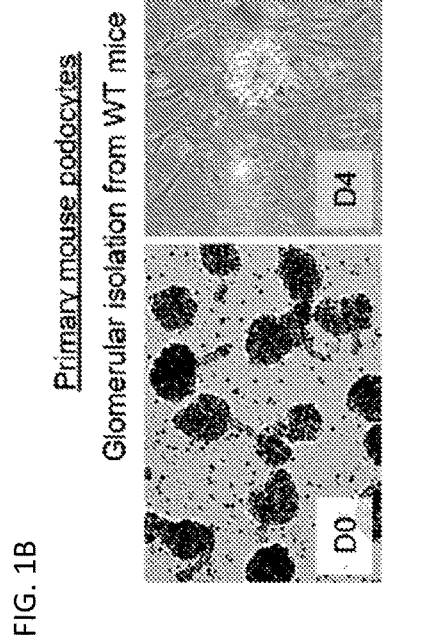
Figure 1A:
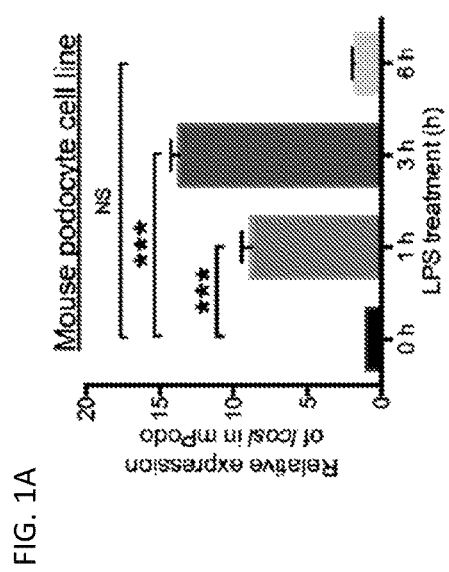

Increased ICOSL expression is an early cellular response to renal injury. Earlier work by Swallow et al. suggested that Icosl mRNA expression was not limited to hematopoietic cells and showed that expression was high in mouse kidney and testes after stimulation by LPS injection (15). We confirmed and extended these observations using cultured renal cells (podocytes and proximal tubules). Inflammatory signals such as LPS and tumor necrosis factor alpha (TNF-α) induced changes in ICOSL expression in renal cells. Icosl mRNA expression was significantly increased in both renal cell types, reaching a peak 3 hours after LPS treatment, followed by a dramatic decrease 6 hours after injection (FIG. 1A). In particular, mouse podocytes (both primary and conditionally immortalized cells) significantly increased Icosl expression in response to LPS stimulation (FIG. 1, A and B). Similar results were observed in human podocytes or when cells were treated with TNF-α (FIG. 1, C and D). Antibody staining showed that LPS-treated human podocytes displayed significantly elevated levels of ICOSL protein (FIG. 1, E and F). Consistently, renal biopsies from patients with FSGS and DN, diseases where the primary lesion involves morphological damage to podocytes in the form of foot process effacement leading to proteinuria, displayed robust glomerular ICOSL expression at early stages of the disease followed by a drastic decline at later stages. This decline mirrored the loss of the podocyte marker protein synaptopodin (ref. 23 and FIG. 1, G-I). These findings imply that increased ICOSL is an early cellular response to renal injury.

Figure 2G:
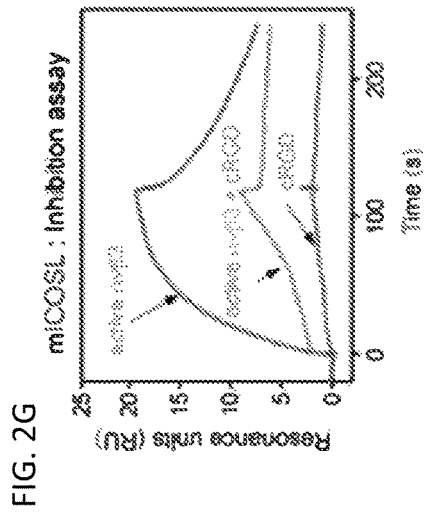
Figure 2E:
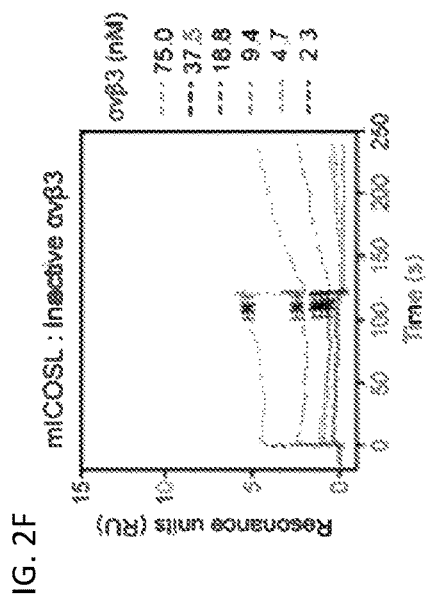
Figure 2F:
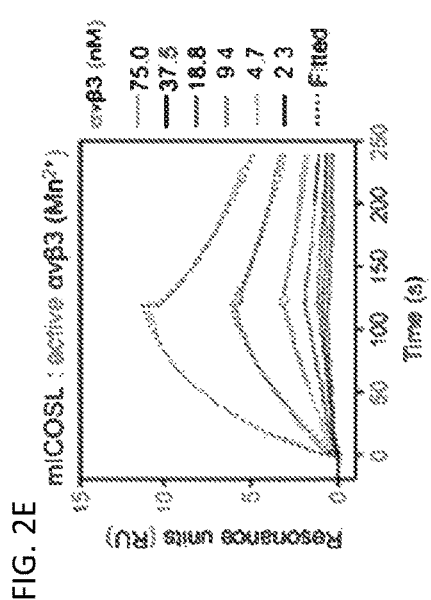
Figure 2H:
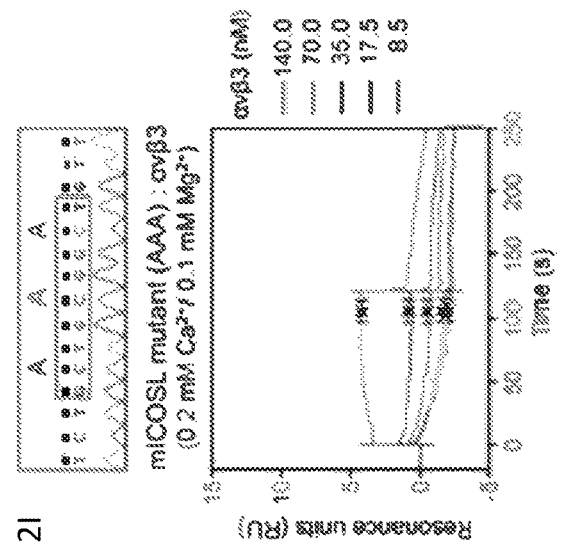
Figure 2I:
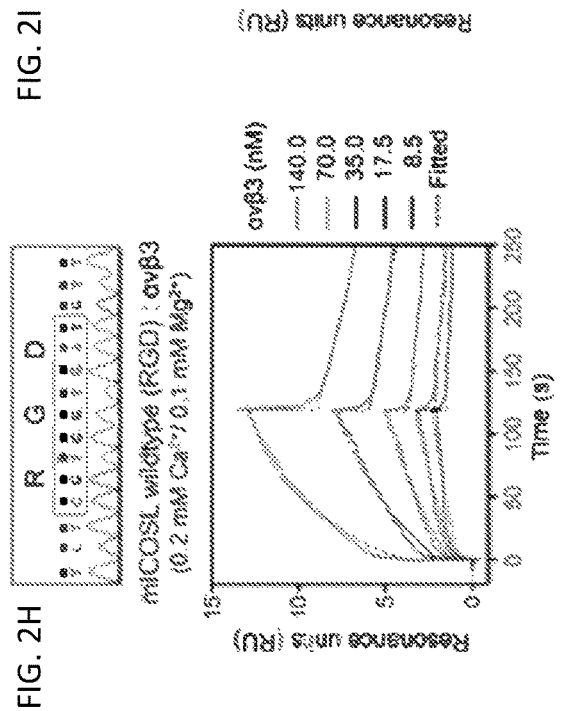
Figure 4B:
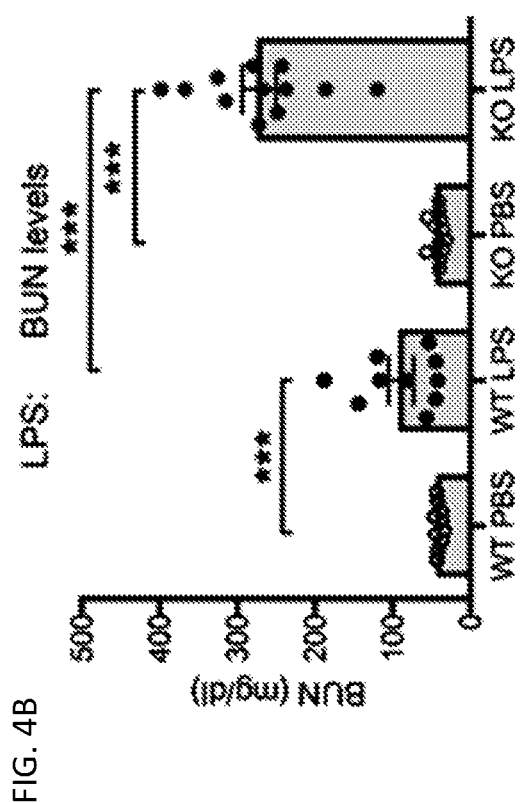
FIGS. 4A-4F illustrate that ICOSL plays a protective role during kidney injury.
Figure 4D:
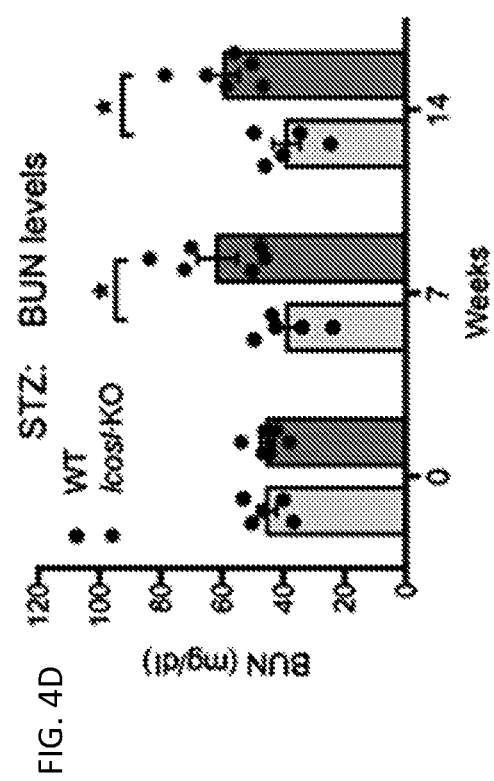
Figure 4A:
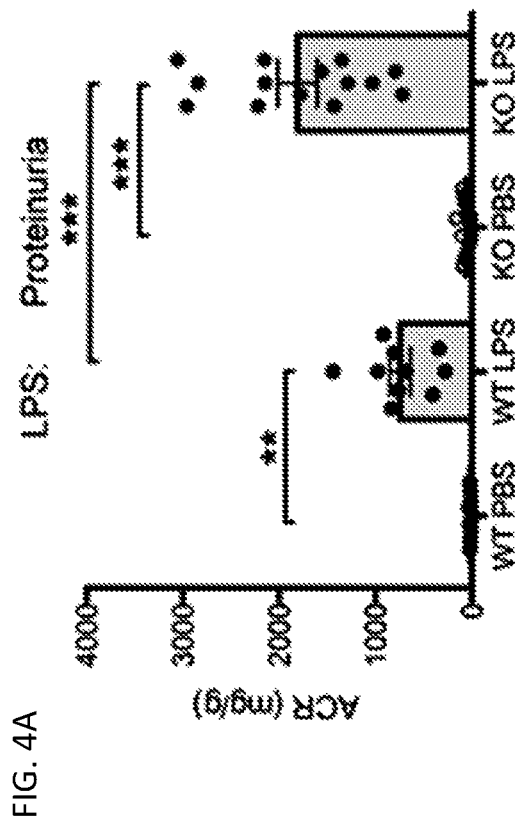
Figure 4C:
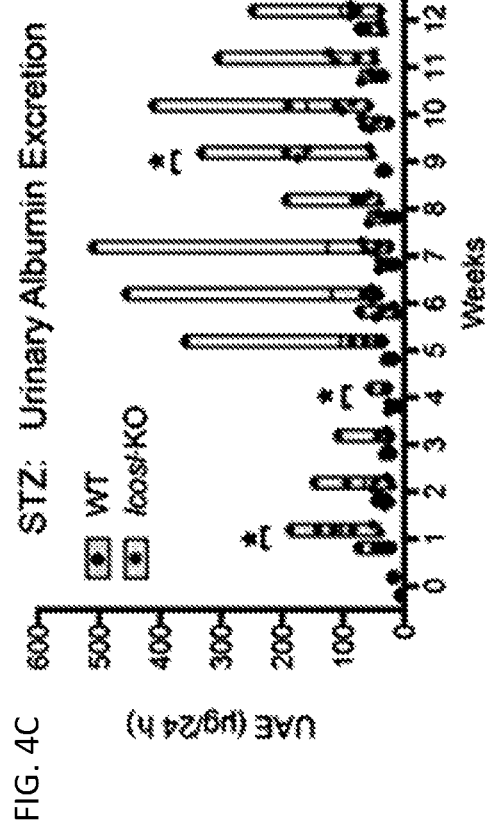
Figures 4E, 4F:

ICOSL protein is a ligand for αvβ3 integrin. An in silico analysis showed that ICOSL contains an RGD sequence, a known integrin-binding motif, unlike other B7 family members (such as B7.1, B7.2, and PDL-1). Multiple alignments of ICOSL protein sequences indicate that the RGD motifs were highly conserved across different species. ICOSL is a transmembrane protein composed of a membrane-distal IgV domain, a membrane-proximal IgC domain, and a cytoplasmic domain. In evolutionarily advanced vertebrates such as human, chimpanzee, monkey, and wolf, the RGD sequences are located in the IgV domain. In contrast, mouse ICOSL has its RGD domain in the IgC domain. 3D homology modeling revealed that both human and mouse ICOSL contain an RGD motif at an exposed loop region, indicating that this RGD motif is accessible to integrin and potentially functional. We performed SPR analysis (FIG. 2A) to determine the binding affinity between recombinant ICOSL protein and αvβ3 or a3B1 integrin, the 2 major integrins expressed on podocytes (2). We first sought to determine if the ICOSL protein could directly bind to αvβ3, an RGD-dependent integrin, in the presence of Mn2+, a potent activator of integrin (9). ICOSL, but not the RGD-lacking B7.1, exhibited high-binding affinity for active αvβ3 integrin ($K_D$=16.2±4.0 nM for human, $K_D$=24.2±6.5 nM for mouse; FIG. 2, B and E). However, the binding affinity was significantly lower when αvβ3 integrin was in its inactive form ($K_D$=412±164 nM for human, $K_D$≥2 mM for mouse; FIG. 2, C and F). Addition of synthetic cyclic RGD (cRGDfv) outcompeted ICOSL-integrin interactions, suggesting that the binding site on ICOSL was indeed the RGD sequence (FIG. 2, D and G). In contrast to αvβ3, α3β1, an RGD-independent laminin-binding integrin, showed no appreciable binding to ICOSL (KD≥2 mM). As expected, the well-characterized traditional binding partner for ICOSL, ICOS, displayed a high binding affinity (KD=5.0±1.4 nM). Next, we tested if ICOSL could bind to αvβ3 integrin in the presence of the physiologically relevant divalent ions Ca2+ and Mg2+. Similar to when Mn2+ is present, ICOSL exhibited high binding affinity for αvβ3 integrin (KD=21.3±1.2 nM; FIG. 2H) at low concentrations (0.2 mM Ca2+ and 0.1 mM Mg2+), a condition in which integrin activation is normally increased (24, 25). However, this strong binding affinity was greatly decreased (KD=400±40 nM) under normal resting serum concentrations of Ca2+ (2 mM) and Mg2+ (1 mM), consistent with our findings that ICOSL preferentially bound to the active form of αvβ3 rather than to the inactive one. To verify that ICOSL interacts with αvβ3 integrin through its RGD motif, we generated RGD-mutated mouse ICOSL protein and assessed its ability to bind mouse αvβ3 integrin (FIG. 2I). Site-directed mutagenesis was used to replace the RGD motif with the amino acids AAA in mouse ICOSL. DNA sequencing was performed to confirm the change (FIG. 2, H and I, top). Indeed, the binding affinity of ICOSL toward αvβ3 was markedly lower when the RGD sequences were mutated to AAA (KD=0.83±0.80 mM; FIG. 2I). These results indicate that the RGD motif in ICOSL is critically important for binding to active αvβ3 integrin. We further tested ICOSL's binding specificity toward other RGD-binding integrins, αIIbβ3 and αvβ5. Interestingly, ICOSL, despite the presence of an RGD motif on these integrins, selectively bound to αvβ3 but not to αIIbβ3 or to αvβ5. Together, these data suggest that ICOSL preferentially binds to active αvβ3 with high affinity through its RGD motif, rather than to other integrins such as α3β1, αIIbβ3, and αvβ5.

ICOSL regulates αvβ3 integrin-dependent adhesion in human podocytes. To investigate the role of ICOSL-αvβ3 integrin pairing in podocyte function, we employed an adhesion assay using cultured human podocytes (FIG. 3A). In line with the selective binding of ICOSL to active αvβ3, podocyte adhesion to ICOSL-coated plates was significantly increased when αvβ3 was activated by Mn2+, and it was completely inhibited by either cRGDfv or anti-β3 antibodies (FIG. 3, B and C). We observed comparable results when podocytes were grown on plates coated with the RGD-containing extracellular matrix protein vitronectin (FIG. 3D). Additionally, ICOSL knock down led to significantly decreased αvβ3-mediated adhesion on vitronectin-coated surfaces, but showed no difference on collagen I-coated plates. Glycosylation, a common posttranslational modification, often alters the structure and function of proteins (24). To determine if ICOSL's glycosylation state impacts its functionality, we evaluated podocyte adhesion to glycosylated or deglycosylated ICOSL. Peptide-N-glycosidase F-treated (PNGaseF-treated) ICOSL produced lower molecular weight bands, representing deglycosylated forms of ICOSL. Our SPR data (FIG. 2E and additional data not shown) closely mirrored our adhesion assay data, indicating that glycosylation state does not affect ICOSL's ability to bind active αvβ3 nor does it affect the adhesive behavior of podocytes. Our data suggest that ICOSL's RGD motif is functionally active and important for αvβ3 integrin-mediated podocyte adhesion, regardless of glycosylation state.

ICOSL plays a protective role during kidney injury. To test ICOSL's contribution to kidney function, we induced kidney injury using 2 different in vivo mouse models: LPS-induced acute kidney damage and streptozotocin-induced (STZ-induced) DN. Using previously reported methods (25), Icosl-KO mice treated with LPS displayed high mortality rates (80%, data not shown), indicating that these mice are vulnerable to LPS-induced kidney damage. Using reduced LPS doses, albumin-to-creatinine ratio (ACR) and blood urea nitrogen (BUN) measurements taken 24 hours after injection showed that Icosl-KO mice exhibit a significant loss in kidney function (ACR: 1812.1±207.9 µg/mg, BUN: 272.0±21.8 mg/dl) when compared with WT mice (ACR: 746.3±109.5 µg/mg, BUN: 89.5±16.0 mg/dl) (FIG. 4, A and B). Similar results were obtained using the STZ-induced model of DN (FIG. 4, C-F). Interestingly, Icosl-KO mice showed early and severe hyperglycemia after 125 mg/kg STZ injection, a high mortality rate (50%) after 21 days, and significantly high levels of proteinuria. Consistent with LPS injection, Icosl-KO mice were significantly vulnerable to kidney damage caused by STZ injection. To extend the time frame of our study and allow for weekly blood glucose and ACR measurements, WT and Icosl-KO mice were injected with a low dose of STZ (100 mg/kg) (FIG. 4, C and D). The STZ-induced diabetic Icosl-KO mice showed a significant and persistent rapid increase in blood glucose levels when compared with WT diabetic mice. Consistent with the high blood glucose levels, the Icosl-KO mice displayed increased overall proteinuria levels, and BUN levels were elevated at 7 and 14 weeks compared with diabetic WT mice (FIG. 4, C and D). Although there were no histological alterations with light microscopy (data not shown), the kidneys of these Icosl-KO mice had severe podocyte foot process effacement 14 weeks after STZ injection as shown by electronic microscopy (FIG. 4, E and F). Loss of ICOSL accelerates renal function decline in the context of DN. These results raised an interesting possibility that ICOSL may play a protective role in maintaining the integrity of kidney tissue.

Figure 5B:
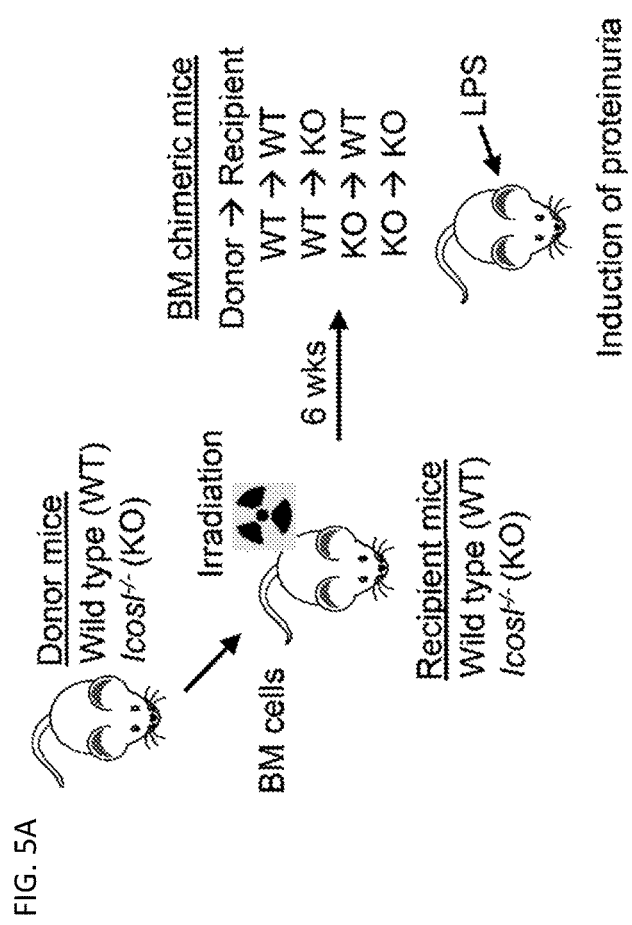
FIGS. 5A-5B illustrate that loss of nonhematopoietic ICOSL aggravates LPS-induced kidney injury.
Figure 5A:
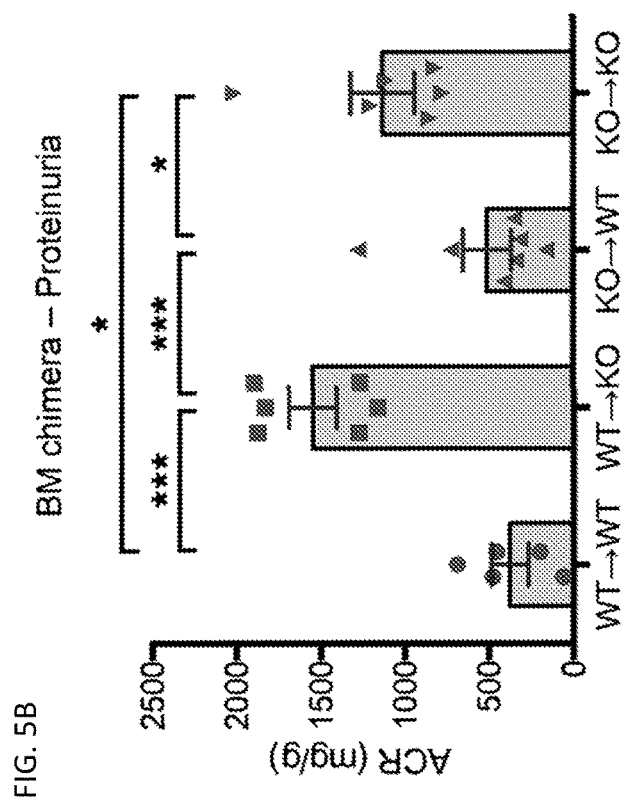

Nonhematopoietic ICOSL protects against LPS-induced kidney injury. We next sought to confirm the renoprotective role of nonhematopoietic ICOSL. Bone marrow (BM) chimeric mice were generated by transferring isolated BM cells from BALB/c WT and Icosl-KO (donor) mice into irradiated WT and/or Icosl-KO (recipient) mice as outlined in FIG. 5A. WT mice given BM cells from WT or Icosl-KO mice exhibited similar ACR levels (WT to WT and KO to WT), whereas Icosl-KO mice given BM cells from either WT or Icosl-KO mice showed significantly higher levels of proteinuria, indicating that nonhematopoietic ICOSL plays an important role in protection against LPS-induced kidney dysfunction (FIG. 5B). To test whether the renoprotective role of ICOSL is independent of its traditional immune-related partner, ICOS, we evaluated the effect of T cell depletion (absence of ICOS) on LPS-induced proteinuria in both WT and Icosl-KO mice. As expected, T cell depletion did not change the ACR levels in either WT or Icosl-KO mice following LPS injection, suggesting that the renoprotective effect of ICOSL is likely not ICOS-dependent.

Figure 6A:
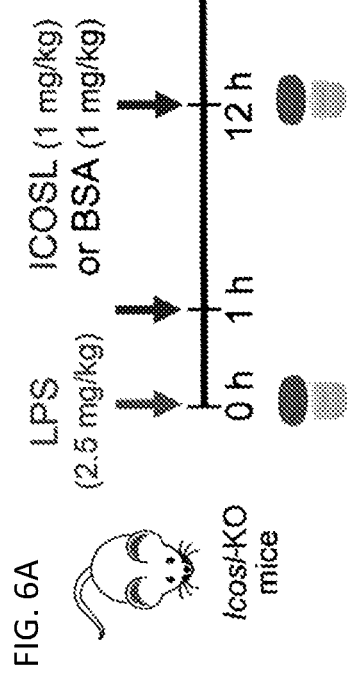
FIGS. 6A-6D illustrate that administration of ICOSL reverses proteinuria in LPS-injected Icosl-KO mice.
Figure 6B:
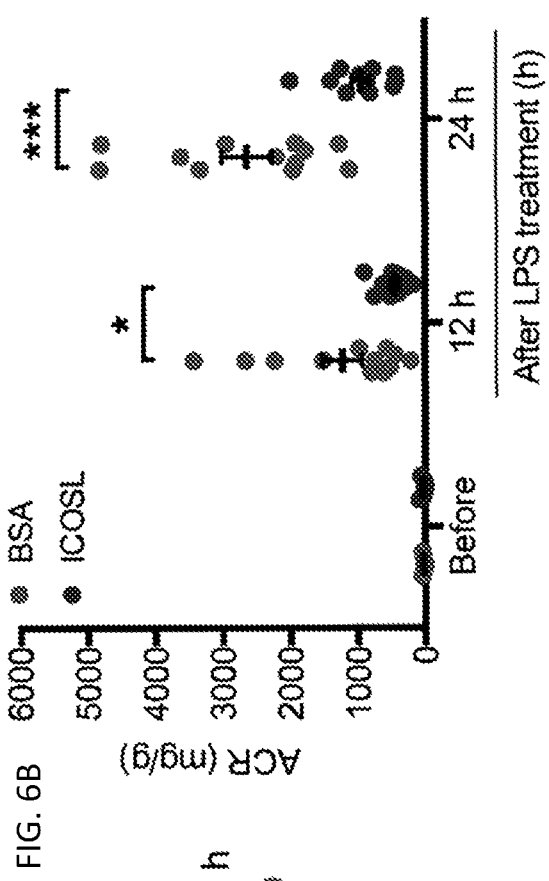
Figure 6C:
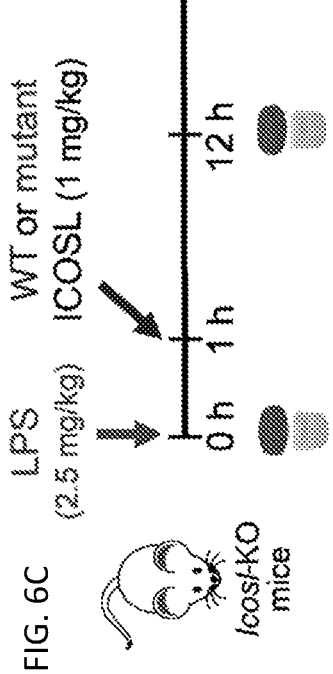
Figure 6D:
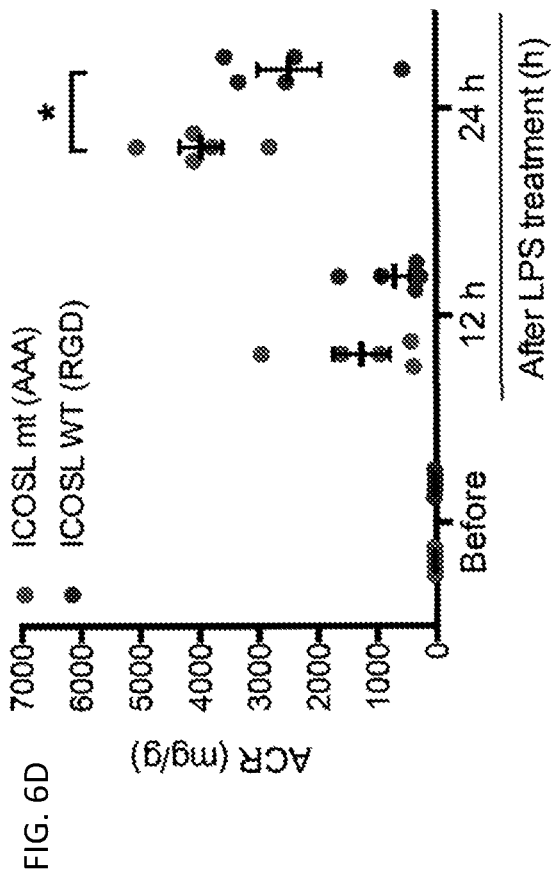

Injection of ICOSL rescues kidney injury in Icosl-KO mice. We tested our hypothesis that ICOSL acts in a renal protective manner by examining the effects of exogenously administering ICOSL protein in Icosl-KO mice that had been subjected to LPS-induced kidney injury. Mice treated with ICOSL protein showed a significant reduction in ACR levels, as compared with controls injected with bovine serum albumin (BSA), both at 12 hours (single ICOSL/BSA dose of 1 mg/kg body weight) and 24 hours (2 ICOSL/BSA doses) after LPS injection (FIG. 6A). The administration of recombinant ICOSL greatly restored kidney function in response to LPS in Icosl-KO (FIG. 6B) and produced similar protective effects in WT mice (FIG. 9). A similar trend of reduced proteinuria was observed when we treated STZ-induced diabetic Icosl-KO mice with the administration of ICOSL twice a week for 4 weeks (P=0.0535, FIG. 8A-8B). To assess the in vivo half-life of exogenously administered ICOSL, we performed plasma pharmacokinetic (PK) analysis for ICOSL after a single intravenously administered dose (1 mg/kg body weight) in Icosl-KO mice. The PK evaluation showed that the mouse that was intravenously injected with ICOSL protein at a dose that provided therapeutic efficacy in rescue experiments (detailed above) exhibited a 2-phase clearance from plasma with a rapid initial clearance (t1/2α=0.06 hour) and a prolonged terminal-phase plasma half-life (t1/2β=18.6 hours). Together, these data strongly suggest that exogenously administered ICOSL, serving as a potential therapeutic option, reverses disease progression and improves kidney function. To further test if the renoprotective effect of ICOSL is dependent on its RGD motif, Icosl-KO mice were treated with either WT (RGD) or mutant (AAA) ICOSL protein using a single dose 1 hour after LPS injection (FIG. 6C). LPS-induced proteinuria was significantly reduced using WT ICOSL but not by mutant protein in Icosl-KO mice (FIG. 6D), supporting our assertion that the RGD sequence on ICOSL is essential for its protective role.

Discussion

Figure 7:
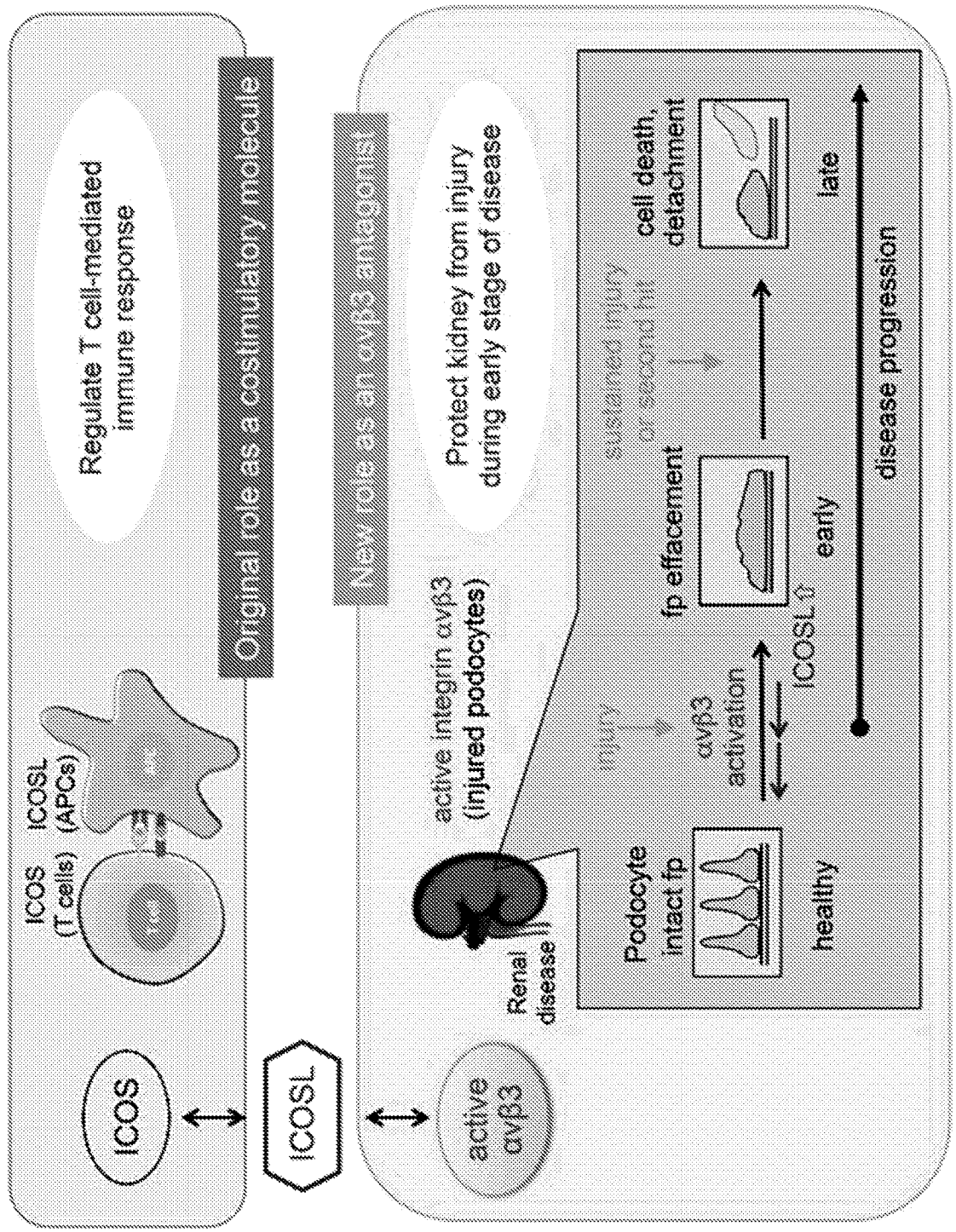
FIG. 7 illustrates a schematic model of ICOSL's functions.

ICOSL is a member of the B7 superfamily of proteins (19, 20) whose study has been limited to outcomes related to its binding with its traditional partner, ICOS. This binding is critical for T cell activation and for the control of T cell-mediated immune responses (15-18). In the present study, we demonstrated that ICOSL bound activated αvβ3 integrin on podocytes and modulated their adhesive characteristics. Our data suggested that this binding provided a mechanism for renoprotection by presumably modulating αvβ3 integrin-dependent signaling (FIG. 7).

As previously mentioned, Odobasic et al. hinted that ICOSL may play a role in lessening the severity of kidney damage in a mouse model of crescentic glomerulonephritis (GN) (21), but this study narrowly focused on direct ICOS-ICOSL interactions within the kidney. What is becoming increasingly evident is that proteins that were once thought to be exclusively part of the immune response are also expressed on and functionally play a role in nonimmune cells. We were prompted to look more closely at ICOSL in the context of kidney disease since its expression was reported to be elevated in the kidney in response to LPS (15). Indeed, our results confirm this finding and we extend the specificity of this expression to the glomerulus in general and to podocytes in particular (FIG. 1). Taking advantage of our expertise with cultured mouse and human podocyte cells as well as primary mouse podocytes, we observed a rapid rise in ICOSL expression in mere hours after an immune stimulus (FIG. 1, A-F). Human biopsy samples showed similar results where glomerular ICOSL expression greatly increased at early stages of kidney disease then dropped at later stages (FIG. 1, G-I). A rapid increase in ICOSL expression at the early stages of kidney injury is in accordance with a previous report that showed a related molecule in the B7 superfamily (B7.1) also increased expression in response to LPS injection (26). To date, all evidence suggests that there is a substantial increase in both ICOSL mRNA and protein expression levels at very early stages of renal pathogenesis. A comprehensive examination of the ICOSL protein structure revealed that unlike other members of the B7 costimulatory family of molecules, ICOSL contained an RGD motif (FIG. 2). A survey of available databases showed that the RGD motif was highly conserved across several different species. This was intriguing, and pointed to the possibility that ICOSL could be functioning within the kidney/podocyte by binding not to its traditional immune-related partner (ICOS), but instead to the well-studied and podocyte-expressed αvβ3 integrin. Our group, along with others, has highlighted the importance of signaling through this integrin (6-9, 12). We subsequently demonstrated direct binding between ICOSL and αvβ3 integrin using the highly sensitive technique of SPR (FIG. 2, C-I). Site-directed mutagenesis combined with SPR analyses revealed that the RGD motif in ICOSL was critically important for binding to αvβ3 integrin (FIG. 2, H and I). Furthermore, our analysis revealed that this binding is (a) highly selective for αvβ3 but not for other integrins such as α3β1, αIIbβ3, and αvβ5 (FIG. 2); (b) dependent on the activation state of αvβ3 integrin (FIG. 2); and (c) relatively strong with a high binding affinity (average KD=10-30 nM). At the cellular level, we confirmed that adhesion of human podocytes to ICOSL protein was dependent on the activation status of αvβ3 integrin (FIG. 3). This set of results points to a mechanism whereby podocytes can mount a fine-tuned response to counterbalance a harmful overactivation of αvβ3 integrin during injury (FIG. 7). This is physiologically relevant because extra-renal immune cells secrete permeability factors such as suPAR, which activate αvβ3 integrin on podocytes, leading to podocyte foot process effacement and the development of proteinuria (25, 27).

The importance of ICOSL's role in protecting the kidney filter was made strikingly clear when we challenged Icosl-KO mice with an inflammatory LPS stimulus, or induced a state of diabetic nephropathy via STZ injection (FIG. 4). In both instances, conventional doses resulted in severe reactions in the KO mice. These experiments revealed the importance of having ICOSL expression, but did not definitively address the question of its source since our KO was global in nature. Being aware of ICOSL's significant and well-documented role as a costimulatory ligand for ICOS in immune-related responses, we set out to determine if the hematopoietic system was involved in the apparent protective affects we observed. Our bone marrow chimera study set out to address this question and showed that induced ICOSL generated from nonlymphoid cells is important in the reduction of proteinuria after LPS-induced kidney injury (FIG. 5). Since it is known that ICOS is exclusively expressed in T cells and its expression is induced upon cell activation, we tested if T cell depletion (resulting in an absence of ICOS) could impact the renoprotective effect of ICOSL. T cell depletion did not change the ACR levels of LPS-injected mice. The results of our rescue experiments (FIG. 6) strongly suggest that ICOSL has the potential to act as a powerful therapeutic option for some forms of kidney disease.

Understanding the mechanisms leading to glomerular injury and the endogenous agents that protect against it could foster the development of precise therapies that stop or delay disease progression. αvβ3 integrin activation is known to be involved in the initiation of glomerular damage (6-11, 28) and is possibly induced by physiological activators such as suPAR and TNF-α. Blocking or abrogating αvβ3 activation via antagonist treatment has been shown to significantly reduce proteinuria, kidney fibrosis, and subsequent disease progression in animal models (6, 7, 12-14). Our studies show that ICOSL is an endogenous protective agent that can counteract αvβ3 integrin activation. The initially elevated ICOSL expression levels diminished in concert with disease progression, and restoration of ICOSL by exogenous application improved renal function in mice (FIG. 6). This is clear evidence that an ICOSL-based therapy is a promising therapeutic strategy to reverse disease progression. However, given that ICOSL is one of many endogenous proteins that are highly prone to enzymatic degradation, improvement of its pharmacokinetic properties is required to enhance efficacy in vivo. Moreover, identification of intrinsic factors and conditions triggering renal ICOSL induction will help effectively and safely target the disease.

αvβ3 integrin is reported to be widely expressed in various cell types other than podocytes, such as endothelial cells, fibroblasts, epithelial cells, osteoblasts, and smooth muscle cells (29). Efficacy of αvβ3 integrin-blocking drugs on a variety of disease conditions will be tested. The binding of ICOSL to αvβ3 integrin, and the resulting modulation of aberrant integrin signaling can be used to provide new therapeutic targets, for example in cell expressing αvβ3 integrin (FIG. 7 and refs. 14, 30).

Our study uncovers that ICOSL, beyond its traditional costimulatory function, protects the kidney filter from injury by serving as a potent endogenous αvβ3-selective antagonist. This newly discovered protective role for ICOSL has allowed us to better understand the pathogenesis of αvβ3 integrin-mediated podocyte damage and offers promising novel avenues to pursue therapeutics for renal disease as well as disease conditions arising from aberrant αvβ3 integrin activation.

Methods

Mice. Icosl-KO mice back-crossed to BALB/c mice as previously described (30) were a gift from Alison Finnegan (Rush University Medical Center, Chicago, Illinois, USA). BALB/c mice were obtained from the Jackson Laboratory. All groups of mice were age- and sex-matched. The number of animals used in each experiment is described in the figure legends.

Reagents. Recombinant proteins used in this study were as follows: human integrin αvβ3 (R&D Systems, 3050-AV), human integrin α3β1 (R&D Systems, 2840-A3), human integrin αIIbβ3 (R&D Systems, 7148-A2), human integrin αvβ5 (R&D Systems, 2528-AV), human fibronectin (R&D Systems, 4305-FNB-200), human ICOSL-His Tag (Thermo Fisher Scientific, 11559H08H50), mouse integrin αvβ3 (R&D Systems, 7889-AV-050), mouse ICOSL (Sino Biological, 50-190-M08H25), human B7.1 (R&D Systems, 140-B1), and human ICOS (R&D Systems, 169-CS). Antibodies used were as follows: mouse anti-human αvβ3 integrin (LM609 clone; Millipore, MAB1976), rabbit anti-His tag (Rockland, 600-401-382), rabbit IgG (Gene Tex, GTX35035), mouse anti-human synaptopodin (D-9; Santa Cruz Biotechnology, sc-515842), rabbit anti-ICOSL (MyBioSource, MBS6004943), and custom polyclonal rabbit anti-ICOSL (GenScript; www.genscript.com; a peptide corresponding to amino acids YPRPNVYWINKTDNC (SEQ ID NO: 3) was conjugated to KLH via an N-terminal cysteine residue and the final serum titer was >1:100,000 by ELISA). Other reagents used in this study were as follows: peptide-N-glycosidase F (PNGaseF; New England Biolabs, P0704S), cyclo [Arg-Gly_Asp-D-Phe-Val] (synthetic cRGD peptide cRGDfV; Biomol, BML-AM100), lipopolysaccharide (LPS) from *E. coli* 0111: B4 (LPS-EB; Invitrogen, tlrl-eblps), streptozotocin (STZ; Sigma-Aldrich, S0130), vitronectin (Molecular Innovations, MVN-417), n-Octyl-β-D-glucopyranoside (Abcam, ab142071), and collagen I from rat tail (Gibco, A10483).

Cell culture. Immortalized human podocytes were cultured at 37° C. for 10-14 days for differentiation as previously described (9). The cells were cultured in RPMI-1640 medium (Gibco, 11875) enriched with 10% fetal bovine serum (FBS; Denville Scientific, FB5001-H), insulin-transferrin-selenium (10.0 µg/ml, 5.5 µg/ml, and 6.7 ng/ml, respectively) supplement (Gibco, 41400045), 100 U/ml penicillin, and 100 µg/ml streptomycin (Gibco, A15140). Immortalized mouse podocytes were cultured according to published protocols (31). Briefly, cells were incubated in tissue culture medium (RPMI-1640 medium with 10% FBS, 100 U/ml penicillin, and 100 µg/ml streptomycin) supplemented with mouse recombinant interferon-γ (Cell Sciences, CR2041), at a concentration of 50 U/ml for the first 2 passages and then 20 U/ml for later passages, in tissue culture flasks coated with collagen I (BD Biosciences, 354236) at 33° C. for proliferation. For differentiation, cells were thermo-shifted to 37° C. and incubated without interferon-γ for 10-14 days. For assays in the 96-well plates, human or mouse cells were differentiated at 37° C. in large tissue culture flasks for 7 days prior to seeding in the appropriate well plates (i.e., 386-well plate for high-content screening assays, FIG. 3A), and subsequently reseeded and incubated in multiwell plates for another 3-4 days. The cells were routinely tested for the presence of mycoplasma, and were allowed to differentiate for 10 days prior to experiments. Immortalized mouse kidney proximal tubule epithelial (TKPTS) cells (32) were obtained from Judit Megyesi (University of Arkansas for Medical Sciences, Little Rock, Arkansas, USA) and cultured in DMEM/Ham's F12 medium (Corning, 15-090-CM) supplemented with 7% FBS, 50 µU/ml insulin (Sigma-Aldrich, 15500), 100 U/ml penicillin, and 100 µg/ml streptomycin at 37° C.

Reverse transcription and quantitative polymerase chain reaction (qPCR) assays. Total RNA was isolated from cells (primary mouse podocytes, cultured mouse and human podocytes) using Trizol reagent (Invitrogen) according to the manufacturer's protocol. cDNAs were synthesized using a High Capacity cDNA Reverse Transcription Kit (Applied Biosystems, 4368813). PCR reactions were performed in triplicate using a CFX96 Real-Time System (Bio-Rad). For analysis, results were expressed as fold changes by LPS/TNF-α treatment using the gene expression levels normalized to those of GAPDH (2-ΔΔCt method). The following TaqMan gene probes purchased from Thermo Fisher Scientific were used: mouse Icosl (Mm00497238_m1), human ICOSLG (Hs00323621_m1), mouse Gapdh (Mn99999915_g1), and human GAPDH (Hs02758991_g1).

Isolation of primary podocytes. Primary mouse podocytes were isolated using Dynabeads magnetic separation as previously described with some modifications (33). Briefly, mice were anesthetized and perfused through the heart with 20 ml Hank's Balanced Salt Solution (HBSS), which contained 8×107 M-450 Dynabeads (Invitrogen, 14013). Kidneys were harvested, minced into small pieces, and digested in HBSS buffer containing 1 mg/ml collagenase A (Sigma-Aldrich, C-6885) and 100 U/ml DNase I (New England Biolabs, M0303L) at 37° C. for 30 minutes. Digested tissue was pressed twice though a 100-µm cell strainer (BD Biosciences, 352360), washed with HBSS buffer, then subjected to magnetic particle isolation. Isolated glomeruli were then ready to be cultured on precoated collagen I dishes for 5 days. Cells were trypsinized and filtered using a 40-µm cell strainer (BD Biosciences, 352340). Filtered cells were spun down and seeded on collagen I-coated dishes for culturing.

Production and transduction of lentivirus. Lenti ORF clone of human ICOSL (RC208975L2) and ICOSL-human shRNA constructs in lentiviral GFP vector (TL303997) targeting human ICOSL mRNA were obtained from Ori- Gene. An empty lentiviral vector and scrambled negative shRNA construct were used as controls. The lentiviral constructs, along with psPAX2 (packaging) and pCMV-VSVG (envelope) vectors, were transfected into HEK-293T cells using Fugene 6 reagent (Promega) according to manufacturer's instructions. A lentivirus harboring ICOSL was collected from the culture media after 3 days, titrated, aliquoted, and then stored at −80° C. Nucleospin RNA virus columns (Macherey-Nagel, 740956) were used for virus RNA isolation and titration was achieved using the Lenti-X qRT-PCR Titration Kit (Clontech, 631235). For transduction of lentivirus, human podocytes were counted (5×105 cells) and plated onto T75 flasks. Twenty-four hours later, growth medium was aspirated and replaced with DMEM media containing lentivirus and incubated overnight. The next day, cells were replaced with complete growth media. Cells were maintained in complete growth media until cell assays were performed 30-48 hours later. Using a triplicate set, the cells were assayed for expression knock down using qRT-PCR.

Homology modeling of human and mouse ICOSL. The 3D models of ICOSL isoform 1 (extracellular domain) were constructed using a homology modeling method (SWISS-MODEL online server) with chain A of 410K (PDB Code, Crystal structure of murine B7-H3, PDL-1 extracellular domain) as a template, which shows the highest sequence identity as 32.2%. Restrained minimization was performed for both structures to optimize the constructed models using the Schrödinger modeling package (minimized on hydrogens first, and then RMSD of heavy atoms converged to less than 0.30 Å in OPLS3 force field).

Adhesion assays and analysis of image quantification. Bovine serum albumin (BSA, 20 g/ml) or human ICOSL (20 µg/ml) was used to coat 348-well plates. Human podocytes were collected from tissue culture flasks and treated with β3 integrin antibody (10 µg/ml), isotype control mouse IgG (10 µg/ml), or cRGD peptide (10 µg/ml) for 15 minutes at 37° C. followed by treatments with MnCl2 (0.25 mM) or the appropriate combination as indicated in FIG. 3A before loading into the precoated 348-well plates (human podocytes: 4000 cells/well; mouse podocytes: 5000 cells/well). After incubating for 30 minutes at 37° C., cells were then washed and fixed using a solution of 4% paraformaldehyde (PFA) in PBS for 20-30 minutes at room temperature. The cells were washed, then if needed, stained with 0.1 µg/ml (in PBS) DAPI (Invitrogen, D1306) or 2 µg/ml (in PBS) Cell-Mask Blue (Invitrogen, H32720) to visualize nuclei and the individual cell boundaries, respectively. For each condition, assays were performed in triplicate for assay robustness. For image analysis, the podocytes were imaged using an Opera high-content image system and quantification was performed using Columbus software (Perkin Elmer) (34). To count adhered podocytes, nuclei were detected using DAPI signal, and the nuclei number was counted. The nuclei number in each well was considered the number of cells adhered.

Mouse and human ICOSL DNA constructs. The mouse full-length Icosl coding sequence (NM_015790, transmembrane protein) was prepared by codon-optimized synthesis for *Escherichia coli* expression (Biobasic). Briefly, the synthesized coding sequence was cloned between the NdeI and XhoI sites of the pET15b expression vector carrying an N-terminal His-Tag sequence (Novagen), verified by sequencing. Primers used for amplifying the human ICOSL coding sequence by PCR were as follows: (NdeI, forward: 5'-ATGCATCATATGCGGCTGGGCAGTCCTGGACT-3' (SEQ ID NO: 4) and XhoI, reverse: 5'-ATG-GATCTCGAGTTAAACGTGGCCAGTGAGCTCTG-3' (SEQ ID NO: 5)). These primers covered whole-protein sequences based on the GenBank sequence NM_015259 and were amplified from a purchased cDNA clone (OriGene, RC208975L2). The purified PCR product was subcloned into pET15b with the indicated enzyme sites and verified by sequencing. Transformation of verified plasmids into BL21 (DE3) cells (Novagen) was performed for protein purification. For mutagenesis on mouse Icosl, mutations were introduced by PCR using the QuickChange Lightning Site-Directed Mutagenesis kit (Agilent Technologies, 210518). The mutagenic oligonucleotides used for AAA mutation from RGD sequence, verified by sequencing, were as follows: forward: 5'-TGCGTCTGCCGTGGACCTCT-GCTGCGGCTGTTCTGTGCTGCGTTG-3' (SEQ ID NO: 6), reverse: 5'-CAACGCAGCACAGAACAGCC-GCAGCAGAGGTCCACGGCAGACGCA-3' (SEQ ID NO: 7).

Purification of mouse and human ICOSL protein. Protein purification was done as previously described (9), with some modifications. Briefly, each mouse and human ICOSL construct was transformed into *Escherichia coli Rosetta*2 (DE3) cells (Novagen). The cells were then induced from an exponentially growing culture by 0.5 mM isopropyl β-D-1-thiogalactopyranoside (IPTG) for 12 hours at 27° C. Cells were harvested and lysed by sonication at 65% amplitude for 100 three-second bursts separated by 6 seconds of off time (Sonic Dismembrator Model 500, Thermo Fisher Scientific) in lysis buffer (B-PER Bacterial Protein Extraction Reagent, Thermo Fisher Scientific, 90084) including 1 mg/ml lysozyme (Thermo Fisher Scientific, 89833), 0.025 mg/ml DNase I (Roche, 11284932001), and protease inhibitor cocktail (Roche, 04693124001). The His-tag fused ICOSL protein was purified using HisTrap HP column (GE Healthcare, 175247) chromatography where Ni-binding buffer (50 mM NaH2PO4, 500 mM NaCl, 10 mM imidazole, and 5 mM β-mercaptoethanol, pH 8.0) was applied to wash unbound impurities, followed by elution with a stepwise gradient using Ni-elution buffer (50 mM NaH2PO4, 500 mM NaCl, 500 mM imidazole, and 5 mM β-mercaptoethanol, pH 8.0). Fractions containing ICOSL were pooled and sequentially loaded into HiTrap QXL anion exchange columns (GE Healthcare). The ICOSL protein was eluted with a stepwise gradient using affinity buffer (50 mM Tris, 40 mM NaCl, 5 mM β-mercaptoethanol, and 0.1% n-Octyl-β-D-glucopyranoside, pH 8.0) and elution buffer (50 mM Tris, 1 M NaCl, 5 mM β-mercaptoethanol, and 0.1% n-Octyl-β-D-glucopyranoside, pH 8.0). Pure ICOSL fractions were combined, concentrated using an Amicon-Ultra-15 column (10,000 NMWL; Millipore), and buffer exchanged into PBS using a Zebra Spin desalting column (Thermo Fisher Scientific, 89889). Purity and concentration were estimated by SDS-PAGE, GelCode blue staining, and NanoDrop spectrophotometer (Thermo Fisher Scientific). Finally, the purified ICOSL protein was aliquoted and flash frozen as protein beads (20 µl each) in liquid nitrogen, then collected into cryovials under liquid nitrogen and stored at −80° C.

Surface plasmon resonance. Protein interactions were measured and analyzed on a Biacore T200 instrument (GE Healthcare) performed at 25° C. as previously described (9). Briefly, to measure the candidate analyte proteins (integrins αvβ3, α3β1, αvβ5, or αIIbβ3) with binding affinities to mouse/human ICOSL protein (isoform 1), the full-length mouse or human ICOSL was immobilized to flow channels 2 and 3 on a CM5 sensor chip using a standard amine-coupling method. Human B7.1 and fibronectin were also used as controls. The ICOSL protein was diluted in 10 mM sodium acetate, pH 4.0, and immobilized after sensor surface activation with 1-Ethyl-3-(3-dimethylaminopropyl) carbodiimide/N-hydroxysuccinimide) (EDC/NHS) with a 7-minute injection followed by ethanolamine blocking on unoccupied surface area. Integrin αvβ3 protein with a series of increasing concentrations (i.e., 0-160 nM at 2-fold dilution) as an analyte was applied to channels at a 20-25 µl/min flow rate at 25° C. The binding experiments were run with HEPES binding buffer (10 mM HEPES, 150 mM NaCl, 0.05% n-Octyl-β-D-glucopyranoside, pH 7.1). For the study of active status of integrin, 2 mM MnCl2 or 0.2 mM CaCl2 and 0.1 mM MgCl2 were added to the HEPES binding buffer. For the study of inactive status of integrin, 3 mM EDTA or 2 mM CaCl2 and 1 mM MgCl2 were added. For inhibition assay, a constant concentration of 3 or 15 µg/ml cRGDfv was preincubated with increasing concentrations of αvβ3 integrin during sample preparation on a plate, and injected following the same procedure as previously described (9). Data were double-referenced with blank (ethanolamine) resonance unit (RU) values on flow channel 1 and zero concentration analyte signal. Sensorgrams were analyzed using the Biacore T200 evaluation software 2.0.3 and RUs were measured during the equilibration phase at each concentration for steady-state affinity fittings. Kinetic fittings were done by 1-to-1 Langmuir binding model embedded within the Biacore T200 evaluation software 2.0.3.

Immunofluorescence microscopy. Prepared human cells were seeded onto glass coverslips (Marienfeld) at 22×10³ cells/ml in 24-well plates overnight. The following day, cells or human biopsy kidney sections from patients with FSGS or DN were rinsed with ice-cold PBS and fixed with 4% PFA for 10 minutes at room temperature followed by permeabilization with 0.1% Triton X-100 for 5 minutes. After washing with PBS twice for 5 minutes each, the coverslips were incubated with blocking buffer in 5% donkey serum (Sigma-Aldrich, D9663) and 0.3 M glycine for 1 hour at room temperature. For single/dual immunofluorescence staining, cells were incubated with custom rabbit anti-ICOSL (20 µg/ml) and/or mouse anti-human synaptopodin (1:300; Santa Cruz Biotechnology, sc-515842) at 4° C. overnight. The cells were washed with cold PBS and incubated with appropriate Alexa Fluor 647-labeled donkey anti-mouse IgG (1:1000; Molecular Probes, A-31571) and/or Alexa Fluor 488-labeled donkey anti-rabbit IgG (1:1000; Molecular Probes, A-21206) secondary antibodies at room temperature for 1 hour. Cells were stained with 0.1 µg/ml (in PBS) DAPI (Invitrogen, D1306). Then cells or tissue sections were examined using an LSM 700 laser scanning fluorescence confocal microscope running ZEN software (Zeiss). Micrographs of structural markers only were adjusted uniformly in Photoshop (Adobe) using the levels function. The confocal micrographs of human kidney biopsies from healthy, early-stage DN, late-stage DN, early-stage FSGS, or late-stage FSGS were analyzed for glomerular expression of ICOSL by manually selecting glomeruli, defined by synaptopodin, as the region of interest. Mean fluorescence intensity (MFI) was measured using ImageJ software (version 1.52a; NIH). Each disease group was normalized to healthy controls and is shown as fold change. Human podocytes were individually defined by tracing cell borders, and analyzed for ICOSL expression using ImageJ software.

Western blot analysis. PNGaseF treatment for deglycosylation of human ICOSL-His Tag protein (Thermo Fisher Scientific) was carried out following manufacturer's instructions. Approximately 50-100 ng of the protein was separated on SDS-PAGE gradient gels (NuPAGE 4%-12% Bis-Tris, Invitrogen) followed by transfer to nitrocellulose membrane (LI-COR Biosciences, 926-31092). Blots were blocked by TBS Odyssey blocking buffer (LI-COR Biosciences, 927-50000) for 2 hours at room temperature. Blots were incubated with primary antibody, rabbit anti-ICOSL (MyBiosource, 1:500), or rabbit anti-His Tag (1:1000) diluted into TBST and TBS Odyssey blocking buffer (1:1) overnight at 4° C. and IRDye 680RD donkey anti-rabbit IgG (H+L) (LI-COR Biosciences, 926-68073) as secondary antibody in TBST for 1 hour at room temperature. The blotted proteins were detected using an Odyssey CLx imaging system (LI-COR Biosciences).

LPS-induced proteinuric mouse model. Proteinuria was induced with a single injection of LPS as previously described (25) with some modifications. Mice were intraperitoneally injected with LPS-EB at a dose of 2.5 mg/kg body weight.

Mouse model of STZ-induced diabetic nephropathy. BALB/c mice (8- to 12-week-old males) and age- and sex-matched Icosl-KO mice were given two injections of STZ (100 or 125 mg/kg body weight) at 4-day intervals as previously described (35). Briefly, the mice were fasted for 4 hours before being injected intraperitoneally with STZ dissolved in citrate buffer (pH 4.5) (Sigma-Aldrich, C8532). One to two weeks after STZ injection, mice with blood glucose values greater than or equal to 200 mg/dl were defined as STZ-induced diabetic mice. Blood glucose levels were assessed weekly. For the measurement of 24-hour urinary albumin excretion (UAE), urine samples were collected using metabolic cages.

Depletion of T cells in vivo. Anti-mouse Thy1.2/CD90.2 (BioXcell, clone 30-H12, 100 µg per mouse) or control rat IgG2a antibody (BioXcell, clone 2A3) was intravenously injected into BALB/c WT and Icosl-KO mice (9- to 10-week-old females and males) 24 hours prior to LPS injection (2.5 mg/kg, i.p.). Twenty-four hours after LPS treatment, the blood samples were collected and labeled with fluorescently conjugated antibodies specific for mouse CD3 (Biolegend, clone 17A2, 100214). Flow cytometric analysis was carried out using a BD LSR II with FACSDiva software (BD Biosciences), and analyzed with FlowJo software V-10 (TreeStar).

Measurement of blood glucose, ACR, and BUN levels. Blood glucose was measured from blood obtained from the tail vein of mice using a FreeStyle Freedom lite glucometer (Abbott Laboratories). Mouse urine samples were collected and urinary albumin and creatinine were measured by mouse albumin ELISA kit (Bethyl Laboratories, E99-134), and creatinine assay kit (Cayman Chemical, 500701), respectively, according to manufacturers' protocols. The ratio of urinary ACR was then calculated. Serum BUN was measured using a colorimetric QuantiChrom Urea assay kit (Bioassay Systems, DIUR 100) according to the manufacturer's protocol.

Generation of bone marrow (BM) chimeric mice. BM isolation was done as previously described (25). BALB/c WT and Icosl-KO recipients (10- to 12-week-old females) were lethally irradiated with 9.5 Gy using a Gammacell 40 exactor (Best Theratronics) and then injected with freshly isolated BM cells from BALB/c WT and Icosl-KO donors (8- to 10-week-old males) (FIG. 5, A and B). Mice were administered antibiotic-treated water. Six weeks after engraftment, LPS (2 mg/kg body weight, i.p.) was injected into BM chimeric mice to induce proteinuria. Twenty-four hours after LPS injection, urine samples were collected and ACR levels were measured.

Rescue experiment. BALB/c WT and Icosl-KO mice (8- to 10-week-old females and males) were treated with purified mouse ICOSL protein (or BSA as a protein control) by intravenous injection at a dose of 1 mg/kg at 1 and 12 hours after LPS administration (2.5 mg/kg body weight, i.p.). Urine samples were collected at 0, 12, and 24 hours after LPS treatment for ACR measurement. To test if the renoprotective effect of ICOSL is dependent on its RGD motif, 8- to 10-week-old female and male Icosl-KO mice were treated with either WT (RGD) or mutant (AAA) ICOSL protein (1 mg/kg body weight, i.v.) at 1 hour following LPS injection (2.5 mg/kg body weight, i.p.). To test the renoprotective effect of ICOSL in a type I diabetic mouse model, 8- to 10-week-old male Icosl-KO mice were given 2 injections of STZ (100 mg/kg body weight) at 4-day intervals. Two weeks after the first STZ injection, the mice were divided into 2 groups for the interventional study. Each group (n=6/group) was treated with either mouse ICOSL protein (1 mg/kg, i.p., twice/week) or BSA as a protein control for 4 weeks. For the measurement of urinary albumin excretion, urine samples were collected using metabolic cages at 6 weeks after STZ administration (ICOSL/BSA treatment for 4 weeks).

ICOSL protein labeling and pharmacokinetic (PK) analysis. Fluorescently labeled ICOSL protein was generated by using Alexa Fluor (AF) 488 Protein Labeling Kit (Thermo Fisher Scientific, A10235) following manufacturer's instructions. Briefly, the purified mouse ICOSL protein (1 mg) was diluted in 0.5 ml of 0.1 M sodium bicarbonate buffer (pH 8.3) and transferred to a vial containing amine reactive AF488 and a magnetic stir bar. The reaction mixture was stirred for 1 hour at room temperature and then loaded onto the size-exclusion purification column prewashed with PBS. The fraction containing the labeled protein (ICOSL-AF488 conjugate) was eluted from the column and buffer exchanged into PBS using a Zebra Spin desalting column (Thermo Fisher Scientific, 89889) according to the manufacturer's protocol. To perform the plasma PK analysis for ICOSL, ICOSL-AF488 conjugate levels in the blood circulation were quantitated by measuring fluorescence in serum samples from Icosl-KO mice receiving a single i.v. injection. Briefly, blood samples (about 30-40 µl) were collected from the retro-orbital plexus in Icosl-KO mice (12-week-old females, n=3) at 0.03, 0.5, 1, 3, 6, 9, and 24 hours following an i.v. administration of ICOSL-AF488 conjugate (1 mg/kg body weight). After spinning down the blood samples at 16,000 g for 5 minutes, sera were obtained and diluted 10-fold with PBS. A standard curve (ranging from 0.156-10 µg/ml) was prepared by using serial dilution of the injected ICOSL-AF488 conjugate with PBS containing 10% (vol/vol) control mouse serum. Fluorescence intensities of standards and diluted sera were measured at 485 nm excitation and 528 nm emission using a fluorescence plate reader (BioTek). The data at each time point were analyzed to fit to the equation for 2-phase decay using Prism version 6.0 (GraphPad).

Electron microscopy. Kidneys were dissected from LPS- and STZ-induced BALB/c WT and Icosl-KO mice. Renal tissue was PFA-fixed overnight at 4° C. and postfixed in 1% osmium tetroxide (OsO4) for 1 hour on ice. Tissues were washed, dehydrated, and embedded in Embed 812 Resin (EMS, 14120). Ultrathin kidney sections (70 nm) obtained on the EM UC7 Ultramicrotome (Leica) were placed on Formvar-coated Ni slot grids (EMS, FF-2010-Ni) and stained in 5% uranyl acetate and 0.1% lead citrate. EM micrographs were taken using a Sigma HD VP Electron Microscope (Zeiss). For image analysis, foot process effacement was quantified from TEM micrographs of glomeruli as previously described (36). Briefly, multiple capillary loops were imaged at ×5000 and glomerular basement membrane (GBM) length was measured for 10 different glomeruli from a minimum of 4 mice per condition using ImageJ software (version 1.52a; NIH). To quantify effacement, secondary processes were manually tallied, and the total number of foot processes (FPs) was divided by the total GBM length to calculate FPs per micrometer of GBM.

Statistics. Statistical analysis was calculated using Prism 6.0 software (GraphPad). All P values less than or equal to 0.05 were considered significant (*P<0.05, P<0.01, *P<0.001, ****P<0.0001) and are referred to as such in the text.

Study approval. All animal experiments were carried out according to the NIH's Guide for the Care and Use of Experimental Animals (National Academies Press, 2011), and approved by the Institutional Animal Care and Use Committee (IACUC) at Rush University (Chicago, Illinois, USA). Human biopsy kidney sections from patients with FSGS or DN were purchased in accordance with guidelines on human research and with approval of the Institutional Review Board of Rush University Medical Center (Chicago, Illinois, USA).

Unless otherwise defined, scientific and technical terms used in connection with this disclosure shall have the meanings that are commonly understood by those of ordinary skill in the art. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout this disclosure. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. Generally, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference. As utilized in accordance with this disclosure, the terms defined in this disclosure, unless otherwise indicated, shall be understood to have the meanings as defined herein.

The above Figures and disclosure are intended to be illustrative and not exhaustive. This description will suggest many variations and alternatives to one of ordinary skill in the art. All such variations and alternatives are intended to be encompassed within the scope of the attached claims.

Those familiar with the art may recognize other equivalents to the specific embodiments described herein which equivalents are also intended to be encompassed by the attached claims.

REFERENCES

1. Takada Y, Ye X, Simon S. The integrins. *Genome Biol.* 2007; 8 (5): 215.
2. Pozzi A, Zent R. Integrins in kidney disease. *J Am Soc Nephrol.* 2013; 24 (7): 1034-1039.
3. Kreidberg J A, Symons J M. Integrins in kidney development, function, and disease. *Am J Physiol Renal Physiol.* 2000;279 (2): F233-F242.
4. Fogo A B. Mechanisms of progression of chronic kidney disease. *Pediatr Nephrol.* 2007; 22 (12): 2011-2022.
5. Reiser J, Altintas M M. Podocytes. *F1000Res.* 2016; 5 (F1000 Faculty Rev): 114.
6. Wei C, et al. Circulating urokinase receptor as a cause of focal segmental glomerulosclerosis. *Nat Med.* 2011; 17 (8): 952-960.
7. Wei C, et al. Modification of kidney barrier function by the urokinase receptor. *Nat Med.* 2008;14 (1): 55-63.
8. Staeck O, et al. Recurrent primary focal segmental glomerulosclerosis managed with intensified plasma exchange and concomitant monitoring of soluble urokinase-type plasminogen activator receptor-mediated podocyte β3-integrin activation. *Transplantation.* 2015;99 (12): 2593-2597.
9. Hayek S S, et al. A tripartite complex of suPAR, APOL1 risk variants and αvβ3 integrin on podocytes mediates chronic kidney disease. *Nat Med.* 2017;23 (8): 945-953.
10. Yoo T H, et al. Sphingomyelinase-like phosphodiesterase 3b expression levels determine podocyte injury phenotypes in glomerular disease. *J Am Soc Nephrol.* 2015;26 (1): 133-147.
11. Hayek S S, et al. Soluble urokinase receptor and chronic kidney disease. *N Engl J Med.* 2015;373 (20): 1916-1925.
12. Zhou X, et al. An integrin antagonist (MK-0429) decreases proteinuria and renal fibrosis in the ZSF1 rat diabetic nephropathy model. *Pharmacol Res Perspect.* 2017;5 (5): e00354.
13. Maile L A, Gollahon K, Wai C, Dunbar P, Busby W, Clemmons D. Blocking αVβ3 integrin ligand occupancy inhibits the progression of albuminuria in diabetic rats. *J Diabetes Res.* 2014; 2014:421827.
14. Maile L A, et al. Blocking ligand occupancy of the αVβ3 integrin inhibits the development of nephropathy in diabetic pigs. *Endocrinology.* 2014; 155 (12): 4665-4675.
15. Swallow M M, Wallin J J, Sha W C. B7h, a novel costimulatory homolog of B7.1 and B7.2, is induced by TNF-α. *Immunity.* 1999; 11 (4): 423-432.
16. Ling V, et al. Cutting edge: identification of GL50, a novel B7-like protein that functionally binds to ICOS receptor. *J Immunol.* 2000; 164 (4): 1653-1657.
17. Yoshinaga S K, et al. T-cell co-stimulation through B7RP-1 and ICOS. *Nature.* 1999;402 (6763): 827-832.
18. Wang S, et al. Costimulation of T cells by B7-H2, a B7-like molecule that binds ICOS. *Blood.* 2000;96 (8): 2808-2813.
19. Hutloff A, et al. ICOS is an inducible T-cell co-stimulator structurally and functionally related to CD28. *Nature.* 1999;397 (6716): 263-266.
20. Greenwald R J, Freeman G J, Sharpe A H. The B7 family revisited. *Annu Rev Immunol.* 2005; 23:515-548.
21. Odobasic D, Kitching A R, Semple T J, Holdsworth S R. Inducible co-stimulatory molecule ligand is protective during the induction and effector phases of crescentic glomerulonephritis. *J Am Soc Nephrol.* 2006; 17 (4): 1044-1053.
22. Aicher A, et al. Characterization of human inducible costimulator ligand expression and function. *J Immunol.* 2000; 164 (9): 4689-4696.
23. Barisoni L, Kriz W, Mundel P, D'Agati V. The dysregulated podocyte phenotype: a novel concept in the pathogenesis of collapsing idiopathic focal segmental glomerulosclerosis and HIV-associated nephropathy. *J Am Soc Nephrol.* 1999;10 (1): 51-61.
24. Ohtsubo K, Marth J D. Glycosylation in cellular mechanisms of health and disease. *Cell.* 2006; 126 (5): 855-867.
25. Hahm E, et al. Bone marrow-derived immature myeloid cells are a main source of circulating suPAR contributing to proteinuric kidney disease. *Nat Med.* 2017;23 (1): 100-106.
26. Reiser J, et al. Induction of B7-1 in podocytes is associated with nephrotic syndrome. *J Clin Invest.* 2004; 113 (10): 1390-1397.
27. Hall S S. Omen in the blood. *Science.* 2018; 360 (6386): 254-258.
28. Bitzan M, Babayeva S, Vasudevan A, Goodyer P, Torban E. TNF-α pathway blockade ameliorates toxic effects of FSGS plasma on podocyte cytoskeleton and β3 integrin activation. *Pediatr Nephrol.* 2012; 27 (12): 2217-2226.
29. Felding-Habermann B, Cheresh D A. Vitronectin and its receptors. *Curr Opin Cell Biol.* 1993;5 (5): 864-868.
30. Hamel K M, Cao Y, Olalekan S A, Finnegan A. B cell-specific expression of inducible costimulator ligand is necessary for the induction of arthritis in mice. *Arthritis Rheumatol.* 2014; 66 (1): 60-67.
31. Mundel P, et al. Rearrangements of the cytoskeleton and cell contacts induce process formation during differentiation of conditionally immortalized mouse podocyte cell lines. *Exp Cell Res.* 1997;236 (1): 248-258.
32. Ernest S, Bello-Reuss E. Expression and function of P-glycoprotein in a mouse kidney cell line. *Am J Physiol.* 1995;269 (2 pt 1): C323-C333.
33. Takemoto M, et al. A new method for large scale isolation of kidney glomeruli from mice. *Am J Pathol.* 2002;161 (3): 799-805.
34. Reiser J, Lee H W, Gupta V, Altintas M M. A high-content screening technology for quantitatively studying podocyte dynamics. *Adv Chronic Kidney Dis.* 2017;24 (3): 183-188.
35. Tesch G H, Allen T J. Rodent models of streptozotocin-induced diabetic nephropathy. *Nephrology* (Carlton). 2007; 12 (3): 261-266.
36. Lee H W, et al. Absence of miR-146a in podocytes increases risk of diabetic glomerulopathy via up-regulation of ErbB4 and Notch-1. *J Biol Chem.* 2017;292 (2): 732-747.

The invention claimed is:

1. A method of treating an aberrant activation of αvβ3 integrin comprising:
administering a therapeutically effective amount of inducible co-stimulator ligand (ICOSL) polypeptide to a subject in need thereof, wherein the therapeutically effective amount of ICOSL polypeptide is used to treat a kidney injury.

2. The method according to claim 1, wherein the therapeutically effective amount of ICOSL polypeptide is used to treat kidney injury resulting from podocyte diseases or disorders, proteinuria, glomerular diseases, membranous glomerulonephritis, focal segmental glomerulonephritis, minimal change disease, nephrotic syndromes, pre-eclampsia, eclampsia, kidney lesions, collagen vascular diseases, stress, strenuous exercise, benign orthostatic proteinuria, focal segmental glomerulosclerosis (FSGS), IgA nephropathy, IgM nephropathy, membranoproliferative glomerulonephritis, membranous nephropathy, sarcoidosis, Alport's syndrome, diabetes mellitus, kidney damage due to drugs, Fabry's disease, infections, aminoaciduria, Fanconi syndrome, hypertensive nephrosclerosis, interstitial nephritis, Sickle cell disease, hemoglobinuria, multiple myeloma, myoglobinuria, diabetic nephropathy (DN), lupus nephritis, Wegener's Granulomatosis or Glycogen Storage Disease Type 1.

3. The method according to claim 1, wherein the therapeutically effective amount of ICOSL polypeptide is used to treat FSGS.

4. The method according to claim 1, wherein the therapeutically effective amount of ICOSL polypeptide is used to treat kidney injury resulting from diabetic neuropathy.

5. The method according to claim 1, wherein the ICOSL polypeptide comprises SEQ ID NO: 1 or an active fragment thereof.

6. The method according to claim 1, wherein the ICOSL polypeptide comprises amino acids 1-258 of SEQ ID NO: 1.

* * * * *

SEQUENCE LISTING

<160> NUMBER OF SEQ ID NOS: 7

<210> SEQ ID NO 1
<211> LENGTH: 302
<212> TYPE: PRT

<213> ORGANISM: Homo sapiens

<400> SEQUENCE: 1

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270

Ile Gly Trp Val Cys Arg Asp Arg Cys Leu Gln His Ser Tyr Ala Gly
        275                 280                 285

Ala Trp Ala Val Ser Pro Glu Thr Glu Leu Thr Gly His Val
    290                 295                 300

<210> SEQ ID NO 2
<211> LENGTH: 322
<212> TYPE: PRT
<213> ORGANISM: Mus musculus

<400> SEQUENCE: 2

Met Gln Leu Lys Cys Pro Cys Phe Val Ser Leu Gly Thr Arg Gln Pro
1               5                   10                  15

Val Trp Lys Lys Leu His Val Ser Ser Gly Phe Phe Ser Gly Leu Gly
            20                  25                  30

Leu Phe Leu Leu Leu Leu Ser Ser Leu Cys Ala Ala Ser Ala Glu Thr
        35                  40                  45

Glu Val Gly Ala Met Val Gly Ser Asn Val Val Leu Ser Cys Ile Asp

```
             50                  55                  60
Pro His Arg Arg His Phe Asn Leu Ser Gly Leu Tyr Val Tyr Trp Gln
 65                  70                  75                  80

Ile Glu Asn Pro Glu Val Ser Val Thr Tyr Tyr Leu Pro Tyr Lys Ser
                 85                  90                  95

Pro Gly Ile Asn Val Asp Ser Ser Tyr Lys Asn Arg Gly His Leu Ser
            100                 105                 110

Leu Asp Ser Met Lys Gln Gly Asn Phe Ser Leu Tyr Leu Lys Asn Val
        115                 120                 125

Thr Pro Gln Asp Thr Gln Glu Phe Thr Cys Arg Val Phe Met Asn Thr
    130                 135                 140

Ala Thr Glu Leu Val Lys Ile Leu Glu Glu Val Val Arg Leu Arg Val
145                 150                 155                 160

Ala Ala Asn Phe Ser Thr Pro Val Ile Ser Thr Ser Asp Ser Ser Asn
                165                 170                 175

Pro Gly Gln Glu Arg Thr Tyr Thr Cys Met Ser Lys Asn Gly Tyr Pro
            180                 185                 190

Glu Pro Asn Leu Tyr Trp Ile Asn Thr Thr Asp Asn Ser Leu Ile Asp
        195                 200                 205

Thr Ala Leu Gln Asn Asn Thr Val Tyr Leu Asn Lys Leu Gly Leu Tyr
    210                 215                 220

Asp Val Ile Ser Thr Leu Arg Leu Pro Trp Thr Ser Arg Gly Asp Val
225                 230                 235                 240

Leu Cys Cys Val Glu Asn Val Ala Leu His Gln Asn Ile Thr Ser Ile
                245                 250                 255

Ser Gln Ala Glu Ser Phe Thr Gly Asn Asn Thr Lys Asn Pro Gln Glu
            260                 265                 270

Thr His Asn Asn Glu Leu Lys Val Leu Val Pro Val Leu Ala Val Leu
        275                 280                 285

Ala Ala Ala Ala Phe Val Ser Phe Ile Ile Tyr Arg Arg Thr Arg Pro
    290                 295                 300

His Arg Ser Tyr Thr Gly Pro Lys Thr Val Gln Leu Glu Leu Thr Asp
305                 310                 315                 320

His Ala

<210> SEQ ID NO 3
<211> LENGTH: 15
<212> TYPE: PRT
<213> ORGANISM: Artificial Sequence
<220> FEATURE:
<223> OTHER INFORMATION: ICOSL peptide

<400> SEQUENCE: 3

Tyr Pro Arg Pro Asn Val Tyr Trp Ile Asn Lys Thr Asp Asn Cys
 1               5                  10                  15

<210> SEQ ID NO 4
<211> LENGTH: 32
<212> TYPE: DNA
<213> ORGANISM: Artificial Sequence
<220> FEATURE:
<223> OTHER INFORMATION: ICOSL primer forward

<400> SEQUENCE: 4
atgcatcata tgcggctggg cagtcctgga ct                              32

<210> SEQ ID NO 5
```

```
<211> LENGTH: 35
<212> TYPE: DNA
<213> ORGANISM: Artificial Sequence
<220> FEATURE:
<223> OTHER INFORMATION: ICOSL primer reverse

<400> SEQUENCE: 5
atggatctcg agttaaacgt ggccagtgag ctctg                              35

<210> SEQ ID NO 6
<211> LENGTH: 45
<212> TYPE: DNA
<213> ORGANISM: Artificial Sequence
<220> FEATURE:
<223> OTHER INFORMATION: RGD mutation primer forward

<400> SEQUENCE: 6
tgcgtctgcc gtggacctct gctgcggctg ttctgtgctg cgttg                   45

<210> SEQ ID NO 7
<211> LENGTH: 45
<212> TYPE: DNA
<213> ORGANISM: Artificial Sequence
<220> FEATURE:
<223> OTHER INFORMATION: RGD mutation primer reverse

<400> SEQUENCE: 7
caacgcagca cagaacagcc gcagcagagg tccacggcag acgca                   45
```